United States Patent
Boppart et al.

(10) Patent No.: US 7,725,169 B2
(45) Date of Patent: May 25, 2010

(54) CONTRAST ENHANCED SPECTROSCOPIC OPTICAL COHERENCE TOMOGRAPHY

(75) Inventors: Stephen A. Boppart, Champaign, IL (US); Chenyang Xu, Ayer, MA (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 703 days.

(21) Appl. No.: 11/405,005

(22) Filed: Apr. 14, 2006

(65) Prior Publication Data

US 2006/0285635 A1 Dec. 21, 2006

Related U.S. Application Data

(60) Provisional application No. 60/672,205, filed on Apr. 15, 2005.

(51) Int. Cl.
*A61B 6/00* (2006.01)
(52) U.S. Cl. .................. 600/473; 600/407; 600/477; 356/479; 356/458
(58) Field of Classification Search ............ 356/479, 356/458; 424/490, 130.1, 143.1; 600/407, 600/410, 47, 476, 473
See application file for complete search history.

(56) References Cited

U.S. PATENT DOCUMENTS

| | | | |
|---|---|---|---|
| 4,522,811 A | 6/1985 | Eppstein et al. |
| 4,930,516 A | 6/1990 | Alfano et al. |
| 5,095,487 A | 3/1992 | Meyerhofer et al. |
| 5,199,431 A | 4/1993 | Kittrell et al. |
| 5,247,343 A | 9/1993 | Burch |
| 5,280,788 A | 1/1994 | Janes et al. |
| 5,303,710 A | 4/1994 | Bashkansky et al. |
| 5,362,478 A | 11/1994 | Desai et al. |
| 5,439,686 A | 8/1995 | Desai et al. |
| 5,451,785 A | 9/1995 | Faris |
| 5,459,570 A | 10/1995 | Swanson et al. |
| 5,491,524 A | 2/1996 | Hellmuth et al. |
| 5,498,421 A | 3/1996 | Grinstaff et al. |

(Continued)

FOREIGN PATENT DOCUMENTS

EP 1 154 224 11/2001

(Continued)

OTHER PUBLICATIONS

Invitation to pay additional fees and partial search report dated Apr. 4, 2008 for PCT application No. PCT/US2007/061364.

(Continued)

*Primary Examiner*—Brian Casler
*Assistant Examiner*—Joel M Lamprecht
(74) *Attorney, Agent, or Firm*—Evan Law Group LLC

(57) ABSTRACT

A method of forming an image of a sample includes performing SOCT on a sample. The sample may include a contrast agent, which may include an absorbing agent and/or a scattering agent. A method of forming an image of tissue may include selecting a contrast agent, delivering the contrast agent to the tissue, acquiring SOCT data from the tissue, and converting the SOCT data into an image. The contributions to the SOCT data of an absorbing agent and a scattering agent in a sample may be quantified separately.

23 Claims, 12 Drawing Sheets

U.S. PATENT DOCUMENTS

| | | | |
|---|---|---|---|
| 5,505,932 A | 4/1996 | Grinstaff et al. |
| 5,508,021 A | 4/1996 | Grinstaff et al. |
| 5,512,268 A | 4/1996 | Grinstaff et al. |
| 5,560,933 A | 10/1996 | Soon-Shiong et al. |
| 5,635,207 A | 6/1997 | Grinstaff et al. |
| 5,639,473 A | 6/1997 | Grinstaff et al. |
| 5,648,506 A | 7/1997 | Desai et al. |
| 5,650,156 A | 7/1997 | Grinstaff et al. |
| 5,665,382 A | 9/1997 | Grinstaff et al. |
| 5,665,383 A | 9/1997 | Grinstaff et al. |
| 5,752,518 A | 5/1998 | McGee et al. |
| 5,836,877 A | 11/1998 | Zavislan |
| 5,891,619 A | 4/1999 | Zakim et al. |
| 5,914,806 A | 6/1999 | Gordon, II et al. |
| 5,921,926 A | 7/1999 | Rolland et al. |
| 5,930,026 A | 7/1999 | Jacobson et al. |
| 5,972,493 A | 10/1999 | Iwasaki et al. |
| 5,994,690 A | 11/1999 | Kulkarni et al. |
| 5,995,645 A | 11/1999 | Soenksen et al. |
| 6,002,476 A | 12/1999 | Treado |
| 6,002,480 A | 12/1999 | Izatt et al. |
| 6,037,579 A | 3/2000 | Chan et al. |
| 6,068,600 A | 5/2000 | Johnson et al. |
| 6,069,932 A | 5/2000 | Peshkin et al. |
| 6,091,496 A | 7/2000 | Hill |
| 6,108,081 A | 8/2000 | Holtom et al. |
| 6,111,645 A | 8/2000 | Tearney et al. |
| 6,134,003 A | 10/2000 | Tearney et al. |
| 6,151,522 A | 11/2000 | Alfano et al. |
| 6,156,292 A | 12/2000 | Quay |
| 6,159,445 A | 12/2000 | Klaveness et al. |
| 6,167,297 A | 12/2000 | Benaron |
| 6,208,886 B1 | 3/2001 | Alfano et al. |
| 6,219,137 B1 | 4/2001 | Vo-Dinh |
| 6,231,834 B1 | 5/2001 | Unger et al. |
| 6,246,892 B1 | 6/2001 | Chance |
| 6,246,901 B1 | 6/2001 | Benaron |
| 6,249,271 B1 | 6/2001 | Albert et al. |
| 6,262,706 B1 | 7/2001 | Albert et al. |
| 6,262,833 B1 | 7/2001 | Loxley et al. |
| 6,264,917 B1 | 7/2001 | Klaveness et al. |
| 6,264,918 B1 | 7/2001 | Johnson et al. |
| 6,280,704 B1 | 8/2001 | Schutt et al. |
| 6,300,932 B1 | 10/2001 | Albert |
| 6,307,633 B1 | 10/2001 | Mandella et al. |
| 6,307,634 B2 | 10/2001 | Hitzenberger et al. |
| 6,312,304 B1 | 11/2001 | Duthaler et al. |
| 6,315,981 B1 | 11/2001 | Unger |
| 6,344,272 B1 | 2/2002 | Oldenburg et al. |
| 6,363,163 B1 | 3/2002 | Xu et al. |
| 6,428,811 B1 | 8/2002 | West et al. |
| 6,485,413 B1 | 11/2002 | Boppart et al. |
| 6,514,767 B1 | 2/2003 | Natan |
| 6,529,277 B1 | 3/2003 | Weitekamp |
| 6,530,944 B2 | 3/2003 | West et al. |
| 6,538,805 B1 | 3/2003 | Norwood et al. |
| 6,539,156 B1 | 3/2003 | Dickson et al. |
| 6,560,478 B1 | 5/2003 | Alfano et al. |
| 6,564,087 B1 | 5/2003 | Pitris et al. |
| 6,574,401 B2 | 6/2003 | Neuberger et al. |
| 6,584,335 B1 | 6/2003 | Haar et al. |
| 6,615,063 B1 | 9/2003 | Ntziachristos et al. |
| 6,618,423 B1 | 9/2003 | Dekorsy et al. |
| 6,689,067 B2 | 2/2004 | Sauer et al. |
| 6,690,966 B1 | 2/2004 | Rava et al. |
| 6,795,777 B1 | 9/2004 | Scully et al. |
| 6,825,928 B2 | 11/2004 | Liu et al. |
| 6,839,586 B2 | 1/2005 | Webb |
| 6,922,583 B1 | 7/2005 | Perelman et al. |
| 7,181,266 B2 | 2/2007 | Frangioni et al. |
| 7,198,777 B2 | 4/2007 | Boppart et al. |
| 7,217,410 B2 | 5/2007 | Suslick et al. |
| 7,610,074 B2 | 10/2009 | Boppart et al. |
| 2002/0028993 A1 | 3/2002 | Hainfeld |
| 2002/0054912 A1 | 5/2002 | Kim et al. |
| 2002/0087071 A1 | 7/2002 | Schmitz et al. |
| 2002/0168161 A1 | 11/2002 | Price et al. |
| 2003/0045798 A1 | 3/2003 | Hular et al. |
| 2003/0068496 A1 | 4/2003 | Wei et al. |
| 2003/0082104 A1 | 5/2003 | Mertelmeier |
| 2003/0171678 A1 | 9/2003 | Batten et al. |
| 2004/0015062 A1 | 1/2004 | Ntziachristos et al. |
| 2004/0023415 A1 | 2/2004 | Sokolov et al. |
| 2004/0024307 A1 | 2/2004 | Golman et al. |
| 2004/0058458 A1 | 3/2004 | Anker et al. |
| 2004/0186359 A1 | 9/2004 | Beaudoin et al. |
| 2004/0249268 A1 | 12/2004 | Da Silva |
| 2005/0004453 A1 | 1/2005 | Tearney et al. |
| 2005/0036150 A1* | 2/2005 | Izatt et al. .................. 356/479 |
| 2005/0078363 A1 | 4/2005 | Gugel |
| 2005/0149002 A1 | 7/2005 | Wang et al. |
| 2005/0168735 A1 | 8/2005 | Boppart et al. |
| 2005/0171433 A1 | 8/2005 | Boppart et al. |
| 2006/0039004 A1 | 2/2006 | De Boer et al. |
| 2006/0066848 A1 | 3/2006 | Frankel |
| 2006/0109478 A1 | 5/2006 | Tearney et al. |
| 2006/0192969 A1 | 8/2006 | Marks et al. |
| 2006/0281068 A1 | 12/2006 | Maier et al. |
| 2006/0292839 A1 | 12/2006 | Yi et al. |
| 2007/0203404 A1 | 8/2007 | Zysk et al. |
| 2008/0140341 A1 | 6/2008 | Ralston et al. |
| 2008/0281205 A1* | 11/2008 | Naghavi et al. .............. 600/458 |
| 2009/0185166 A1 | 7/2009 | Oldenburg et al. |
| 2009/0185191 A1 | 7/2009 | Boppart et al. |
| 2009/0221920 A1 | 9/2009 | Boppart et al. |

FOREIGN PATENT DOCUMENTS

| | | |
|---|---|---|
| EP | 1 312 912 | 5/2003 |
| EP | 1 447 043 | 8/2004 |
| EP | 0 963 540 | 3/2006 |
| WO | WO 90/01697 | 2/1990 |
| WO | WO 97/32182 | 9/1997 |
| WO | WO98/30873 | 7/1998 |
| WO | WO 98/38907 | 9/1998 |
| WO | WO99/06794 | 2/1999 |
| WO | WO99/58972 | 11/1999 |
| WO | WO 00/42906 | 7/2000 |
| WO | WO 00/42912 | 7/2000 |
| WO | WO02/41760 | 5/2002 |
| WO | WO 02/088705 | 11/2002 |
| WO | WO03/061454 | 7/2003 |
| WO | WO2005/028663 | 3/2005 |
| WO | WO2006/020302 | 2/2006 |
| WO | WO2006/032009 | 3/2006 |
| WO | WO2006/099191 | 9/2006 |
| WO | WO2006/135628 | 12/2006 |
| WO | WO 2007/027194 | 3/2007 |
| WO | WO 2007/090147 | 9/2007 |
| WO | WO 2008/008774 | 1/2008 |

OTHER PUBLICATIONS

Sadtler et al., "Spherical ensembles of gold nanoparticles on silica: electrostatic and size effects", Chem. Commun., 1604-05, 2002.

Tearney et al., "High-Speed Phase- and Group-Delay Scanning with a Grating-Based Phase Control Delay Line", Optics Letters, vol. 22, No. 23 :1811-1813, 1997.

Tearney et al., "In vivo endoscopic optical biopsy with optical coherence tomography", Science, 276: 2037-2039, 1997.

Tearney et al., "Rapid acquisition of in vivo biological images by use of optical coherence tomography", Optics Letters, 21: 1408-1410, 1996.

Tearney et al., "Scanning single-mode fiber optic catheter-endoscope for optical coherence tomography", Optics Letters, 21: pp. 543-545, 1996.

Templeton et al., "Monolayer-protected cluster molecules", Acc. Chem. Res., 33:27-36, 2000.

Timmerman et al., "Resorcinarenes" Tetrahedron, 52:2663-704, 1996.

Tkachenko et al., "Multifunctional Gold Nanoparticle-Peptide Complexes for Nuclear Targeting", J. Am. Chem. Soc., 125:4700-4701, 2003.

Wang et al., "Use of a Laser Beam with an Oblique Angle of Incidence to Measure the Reduced Scattering Coefficient of a Turbid Medium", Applied Optics, 34:2362-2366, 1995.

Webb et al., "Sonochemically produced fluorocarbon microspheres: a new class of magnetic resonance imaging agent", J. Magnetic Resonance Imaging, 6:675-683, 1996.

Wei et al., "Resorcinarene-encapsulated nanoparticles: building blocks for self-assembled nanostructures", J. Inclusion Phenomenal Macrocyclic Chemistry, 41, 83-86, 2001.

Wei et al., "Synthesis and Characterization of Resorcinarene-Encapsulated Nanoparticles", Mater. Res. Soc., Symp. Proc. Ser., 581:59-63, 1999.

Wei et al., "Tunable Surface-Enhanced Raman Scattering from Large Gold Nanoparticle Arrays", ChemPhysChem., 2:743-45, 2001.

Wong et al., "Sonochemically produced hemoglobin microbubbles", Mat. Res. Soc. Symp. Proc., 372:8994, 1995.

Zaheer et al., "In vivo near-infrared fluorescence imaging of osteoblastic activity", Nature Biotechnology, 19:1148-54, 2001.

Marks et al., "Interferometric differentiation between resonant Coherent Anti-Stokes Raman Scattering and nonresonant four-wave-mixing processes", arXiv:physics/0403007, pp. 1-8, 2004.

Vinegoni et al., "Nonlinear optical contrast enhancement for optical coherence tomography", Optics Express, vol. 12, No. 2, p. 331-341, 2004.

Kee et al., "Simple approach to one-laser, broadband coherent anti-Stokes Raman scattering microscopy", Optics Letters, vol. 29, No. 23, p. 2701-2703, 2004.

Kano et al., "Vibrationally resonant imaging of a single living cell by supercontinuum-based multiplex coherent anti-Stokes Raman scattering microspectroscopy", Optics Express, vol. 13, Issue 4, pp. 1322-1327, 2005.

Gao et al., "Formulation, Characterization, and Sensing Applications of Transparent Poly(vinyl alcohol)-Polyelectrolyte Blends", Chem. Mater., 10, pp. 2481-2489, 1998.

Marks et al., Molecular Species Sensitive Optical Coherence Tomography Using Coherent Anti-Stokes Raman Scattering Spectroscopy, Coherence Domain Optical Methods and Optical Coherence Tomography in Biomedicine VII, Proceedings of SPIE, vol. 4956, pp. 9-13, 2003.

Bredfeldt et al., "Non-linear interferometric vibrational imaging", Conference on Lasers and Electro-optics, CLEO '03, pp. 309-311, 2003.

Vinegoni et al., "Nonlinear optical contrast enhancement for optical coherence tomography", http://www.arxiv.org/abs/physics/0312114, 13 pages (2003).

Zumbusch et al., "Three-dimensional vibrational imaging by coherent anti-Stokes Raman scattering", Phys. Rev. Lett., 82(20), pp. 4142-4145, 1999.

Cheng et al., "An epi-detected coherent anti-Stokes Raman scattering (E-CARS) microscope with high spectral resolution and high sensitivity", J. Phys. Chem, 105(7), pp. 1277-1280, 2001.

Hashimoto et al., "Molecular vibration imaging in the fingerprint region by use of coherent anti-Stokes Raman scattering microscopy with a collinear configuration", Opt. Lett., 25(24), pp. 1768-1770, 2000.

Volkmer et al., "Vibrational imaging with high sensitivity via epidected coherent anti-Stokes Raman scattering microscopy", Phys. Rev. Lett., 87(2):023901-1-4, 2001.

Fantini et al., "Assessment of the size, position, and optical properties of breast tumors in vivo by noninvasive optical methods", Applied Optics, vol. 37, pp. 1982-1989, 1998.

Faber et al., "Quantitative measurement of attenuation coefficients of weakly scattering media using optical coherence tomography", Optics Express, 12(19), pp. 4353-4365, 2004.

Fujimoto et al., "Optical Coherence Tomography: An Emerging Technology for Biomedical Imaging and Optical Biopsy", Neoplasia, 2(1-2), pp. 9-25, 2000.

Zysk et al., "Computational methods for analysis of human breast tumor tissue in optical coherence tomography images", Journal of Biomedical Optics, 11(5), 054015-1-054015-7, 2006.

Levitz et al., "Determination of optical scattering properties of highly-scattering media in optical coherence tomography images", Optics Express, 12(2), pp. 249-259, 2004.

Morgner et al., "Spectroscopic optical coherence tomography", Optics Letters, 25(2), pp. 111-113, 2000.

Gossage et al., "Texture analysis of optical coherence tomography images: feasibility for tissue classification", Journal of Biomedical Optics, 8(3), pp. 570-575, 2003.

Zvyagin et al., "Refractive index tomography of turbid media by bifocal optical coherence refractometry", Optics Express, 11(25), pp. 3503-3517, 2003.

Gottschalk, "Ein Meβverfahren zur Bestimmung der optischen Parameter biologisher Gewebe in vitro", Dissertation 93 HA 8984, Universität Fridericiana Karlsruhe, 1993.

Bolin, F.P. et al., "Refractive index of some mammalian tissues using a fiber optic cladding method", Applied Optics, 28, pp. 2297-2303, 1989.

Tearney et al., "Determination of the refractive index of highly scattering human tissue by optical coherence tomography", Optics Letters, 20(21), pp. 2258-2260, 1995.

Zysk et al., "Needle-based refractive index measurement using low-coherence interferometry", Optics Letters, 32, pp. 385-387, 2007.

Zysk et al., "Refractive index of carcinogen-induced rat mammary tumours", Phys. Med. Biol., 51, pp. 2165-2177, 2006.

Li et al., "Measurement method of the refractive index of biotissue by total internal reflection", Applied Optics, 35, pp. 1793-1795, 1996.

Knuttel et al., "Spatially confined and temporally resolved refractive index and scattering evaluation in human skin performed with optical coherence tomography", Journal of Biomedical Optics, 5, pp. 83-92, 2000.

Boppart et al., "Optical coherence tomography: feasibility for basic research and image-guided surgery of breast cancer", Breast Cancer Research and Treatment, vol. 84, pp. 85-97, 2004.

Liberman et al., "Palpable breast masses: Is there a role for percutaneous image-guided core biopsy?", American Journal of Roentgenology, vol. 175, pp. 779-787, 2000.

Bolivar et al., "Stereotaxic core needle aspiration biopsy with multiple passes in nonpalpable breast lesions", Acta Radiologica, vol. 39, pp. 389-394, 1998.

Acheson et al., "Histologic correlation of image-guided core biopsy with excisional biopsy of nonpalpable breast lesions", Archives of Surgery, vol. 132, pp. 815-821, 1997.

Pijnappel et al., "The diagnostic accuracy of core biopsy in palpable and non-palpable breast lesions", European Journal of Radiology, vol. 24, pp. 120-123, 1997.

Durduran et al., "Bulk optical properties of healthy female breast tissue", Physics in Medicine and Biology, vol. 47, pp. 2847-2861, 2002.

International Search Report dated Feb. 15, 2007 for International Application No. PCT/US2006/006618, 5 pages.

Marks et al., "Interferometric differentiation between resonant coherent anti-Stokes Raman scattering and nonresonant four-wave-mixing processes", Applied Physics Letters, vol. 85, No. 23, pp. 5787-5789, 2004.

Marks et al., "Nonlinear Interferometric Vibrational Imaging", Physical Review Letters, vol. 92, No. 12, pp. 123905-1-123905-4, 2004.

Boppart et al., "Contrast Enhancement Methods for Optical Coherence Tomography", Biophotonics/Optical Interconnects and VLSI Photonics/WBM Microactivities, 2004 Digest of the Leos Summer Topical Meetings, San Diego, CA, pp. 14-15, 2004.

Marks et al., "Pulse Shaping Strategies for Nonlinear Interferometric Vibrational Imaging Optimized for Biomolecular Imaging", Proceedings of the 26th Annual International Conference of the IEEE EMBS, San Francisco, CA, pp. 5300-5303, 2004.

Bredfeldt et al., "Nonlinear interferometric vibrational imaging of molecular species", Proc. Of SPIE, vol. 5321, pp. 149-156, 2004.

Easy Core Biopsy System, Product Brochure, Boston Scientific, 5 pages, 2004.

Yodh et al., "Spectroscopy and Imaging with Diffusing Light," Physics Today, pp. 34-40, 1995.

Roggan et al., in "Laser Induced Interstitial Thermotherapy", Muller, Ed., pp. 39-40,43, 1995.

Ohmi et al., "In Vitro Simultaneous Measurement of Refractive Index and Thickness of Biological Tissue by the Low Coherence Interferometry", IEEE Transactions on Biomedical Engineering, vol. 47, No. 9, pp. 1266-1270, 2000.

Luo et al., "Optical Biopsy of Lymph Node Morphology using Optical Coherence Tomography", Technology in Cancer Research & Treatment, vol. 4, No. 5, pp. 539-547, 2005.

Dehghani et al., "The effects of internal refractive index variation in near-infrared optical tomography: a finite element modelling approach", Physics in Medicine and Biology, 48, pp. 2713-2727, 2003.

Schmitt et al., "Turbulent nature of refractive-index variations in biological tissue", Optics Letters, vol. 21, No. 16, pp. 1310-1312, 1996.

Zysk et al., "Projected index computed tomography", Optics Letters, vol. 28, No. 9, pp. 701-703, 2003.

Easy Core Biopsy System, Product Brochure, Boston Scientific, 4 pages, 2004.

Evans et al., "Coherent anti-Stokes Raman scattering spectral interferometry: determination of the real and imaginary components of nonlinear susceptibility chi(3) for vibrational microscopy", Optics Letters, vol. 29, No. 24, pp. 2923-2925, 2004.

Yoon et al., "Dependence of line shapes in femtosecond broadband stimulated Raman spectroscopy on pump-probe timed delay", J Chem Phys., 122(2), p. 024505, 2005, 20 pages.

Kolomoitsev et al., "New problems of femtosecond time-domain CARS of large molecules", SPIE vol. 1402, pp. 31-43, 1990.

Mehendale et al, "Towards an anthrax detector using the femtosecond adaptive spectroscopic technique for coherent anti-Stokes Raman Spectroscopy: coherent anti-Stokes Raman spectroscopy signal from dipicolinic acid in bacterial spores", Journal of Modern Optics, vol. 51, pp. 2645-2653, 2004.

Ai et al., "Electrostatic layer-by-layer nanoassembly on biological microtemplates: platelets", Biomacromolecules, 3:560-564, 2002.

Amsden et al., "An examination of factors affecting the size, distribution, and release characteristics of polymer microbeads made using electrostatics", J. Control. Release, 43:183-196, 1997.

Amsden, "The production of uniformly sized polymer microspheres", Pharm. Res., 16:1140-1143, 1999.

Balasubramanian et al., "Extraction and dispersion of large gold nanoparticles in nonpolar solvents", J. Dispers. Sci. Tech. 22:485-89, 2001.

Balasubramanian et al., "Dispersion and stability studies of resorcinarene-encapsulated gold nanoparticles", Langmuir, 18:3676-81, 2002.

Barton et al., "Use of microbubbles as an optical coherence tomography contrast agent", Acad. Radiol, 9, (Suppl 1):552-555, 2002.

Blackwell et al., "New approaches to olefin cross-metathesis", J. Am. Chem. Soc., 122:58-71, 2000.

Boppart et al., "Imaging Developing Neural Morphology Using Optical Coherence Tomography", J. Neuroscience Methods, vol. 70, pp. 65-72, 1996.

Boppart at al., "Investigation of Developing Embryonic Morphology Using Optical Coherence Tomography", Developmental Biology, vol. 177, pp. 54-63, 1996.

Boppart et al., "Noninvasive assessment of the developing Xenopus cardiovascular system using optical coherence tomography", Proc. Natl. Acad. Sci. USA, 94: 4256-4261, 1997.

Boppart et al., "Forward-Imaging Instruments for Optical Coherence Tomography", Optics Letters, vol. 22, No. 21, pp. 1618-1620, 1997.

Boppart et al., "In vivo Cellular Optical Coherence Tomography Imaging", Nature Medicine, vol. 4, No. 7, pp. 861-865, 1998.

Boppart et al., "Intraoperative Assessment of Microsurgery with Three-Dimensional Optical Coherence Tomography", Radiology, vol. 208, pp. 81-86, 1998.

Boppart et al., "Optical Coherence Tomography for Neurosurgical Imaging of Human Intracortical Melanoma", Neurosurgery, vol. 43, No. 4, pp. 834-841, 1998.

Boppart, "Surgical Diagnostics, Guidance, and Intervention Using Optical Coherence Tomography", Ph.D. Thesis, Massachusetts Institute of Technology, Cambridge, MA, 226 pages, 1998.

Boppart et al., "High-Resolution Optical Coherence Tomography-Guided Laser Ablation of Surgical Tissue", J. Surgical Research, 82:275-84, 1999.

Boppart, "Endoscopic Optical Coherence Tomography Imaging of Barrett's Esophagus", M.D. Thesis, Harvard University, 2000.

Bouma et al., "High resolution optical coherence tomographic imaging using a mode-locked $Ti:Al_2O_3$ laser source", Optics Letter, 20:1486-1488, 1995.

Bouma et al., "High-resolution imaging of the human esophagus and stomach in vivo using optical coherence tomography", Gastrointestinal Endoscopy, 51: 467-474, 2000.

Boyer et al., "Photothermal Imaging of Nanometer-Sized Metal Particles Among Scatterers", Science, 297:1160-63, 2002.

Brezinski et al., "Optical Coherence Tomography for Optical Biopsy: Properties and Demonstration of Vascular Pathology", Circulation, vol. 93, pp. 1206-1213, 1996.

Bugaj et al., "Novel fluorescent contrast agents for optical imaging of in vivo tumors based on a receptor-targeted dye-peptide conjugate platform", J. Biomedical Optics, 6:122-33, 2001.

Burns et al., "Tumor-localizing and photosensitizing properties of hematoporphyrin derivative in hamster buccal pouch carcinoma", Oral Surg. Oral Med, Oral Pathol., 61:368-372, 1986.

Cain et al., "Thresholds for Visible Lesions in the Primate Eye Produced by Ultrashort Near-Infrared Laser Pulses", Investigative Ophthalmology & Visual Science, 40:2343-49, 1999.

Cain et al., "Visible Retinal Lesions from Ultrashort Laser Pulses in the Primate Eye", Investigative Ophthalmology & Visual Science, 36:879-888, 1995.

Caruso et al., "Nanoengineering of inorganic and hybrid hollow spheres by colloidal templating", Science, 282:1111-1114, 1998.

Cepak et al., "Preparation and Stability of Template-Synthesized Metal Nanorod Sols in Organic Solvents", J. Phys. Chem. B, 102:9985-90, 1998.

Chen et al., "Noninvasive Imaging of in Vivo Blood Flow Velocity Using Optical Doppler Tomography", Optics Letters, vol. 22, pp. 1119-1121, 1997.

Christiansen et al., "Physical and biochemical characterization of Albunex™, a new ultrasound contrast agent consisting of air-filled albumin microparticles suspended in a solution of human albumin", Biotechnol. Appl. Biochem., 19:307-20, 1994.

Clark et al., "Second harmonic generation properties of fluorescent polymer-encapsulated gold nanoparticles", J. Am. Chem. Soc., 122:10234-35, 2000.

de Boer et al., "Two-Dimensional Birefringence Imaging in Biological Tissue by Polarization-Sensitive Optical Coherence Tomography", Optics Letters, vol. 22, pp. 934-936, 1997.

Decher "Fuzzy Nanoassemblies: Toward Layered Polymeric Multicomposites", Science, 277:1232-1237, 1997.

Desai et al., "Controlled and targeted drug delivery with biocompatible protein shell microspheres", 20th Annual Meeting of Society of Biomaterials, Apr. 4-9, 1994, Boston, MA: Proc. Soc. Biomaterial, 20:112, 1994.

Dick et al., "Computed tomography of experimental liver abscesses using a new liposomal contrast agent", Investigative Radiology, 31:194-203, 1996.

Dowlatshahi et al., "Histologic Evaluation of Rat Mammary Tumor Necrosis by Interstitial Nd:YAG Laser Hyperthermia", Lasers in Surgery and Medicine, 12:159-164, 1992.

Drexler et al., "In vivo Ultrahigh-Resolution Optical Coherence Tomography", Optics Letters, vol. 24, No. 17, pp. 1221-1223, 1999.

El-Sayed "Some interesting properties of metals confined in time and nanometer space of different shapes", Accounts of Chemical Research, 34:257-64, 2001.

Freeman et al., "Self-Assembled Metal Colloid Monolayers: An Approach to SERS Substrates", Science, 267:1629-1632, 1995.
Fu et al., "Visual evidence of acidic environment within degrading poly(lactic-co-glycolic acid) (PLGA) microspheres", Pharmaceutical Research, 17:100-106, 2000.
Fujimoto et al., "Optical biopsy and imaging using optical coherence tomography", Nature Medicine, 1:970-972, 1995.
Gazelle et al., "Nanoparticulate computed tomography contrast agents for blood pool and liver-spleen imaging", Acad. Radiol., 1:373-376, 1994.
Geny et al., "Safety of a new transpulmonary echocontrast agent (Albunex®) in repeated echocardiographic studies in patients", Clin. Cardiol., 20:111-115, 1997.
Gimenez-Conti et al., "The hamster cheek pouch carcinogenesis model", J. Cellular Biochemistry Supplement, 17F:83-90, 1993.
Gram, "Drug absorption and distribution", in Modern Pharmacology with Clinical Applications $5^{th}$ Ed., Craig et al., eds., Little, Brown, & Co., Inc.; Boston, MA, pp. 13-24, 1997.
Grinstaff et al., "Air-filled proteinaceous microbubbles: synthesis of an echo-contrast agent", Proc. Natl. Acad. Sci. USA, 88:7708-7710, 1991.
Grubbs et al., "Ring-Closing Metathesis and Related Processes in Organic Synthesis", Acc. Chem. Res., 28:446-52, 1995.
Haes et al., "A nanoscale optical biosensor: sensitivity and selectivity of an approach based on the localized surface plasmon resonance spectroscopy of triangular silver nanoparticles", J. Am. Chem. Soc., 124:10596-604, 2002.
Handley et al., "Colloidal gold labeling studies related to vascular and endothelial function, hemostasis and receptor-mediated processing of plasma macromolecules", European J. Cell Biology, 43:163-74, 1987.
Handley et al., "Colloidal gold-low density lipoprotein conjugates as membrane receptor probes", Proc. Natl. Acad. Sci. USA, 78:368-71, 1981.
Handley "Methods for Synthesis of Colloidal Gold", Colloidal Gold: Principles, Methods, and Applications, (Academic Press), vol. 1, pp. 13-32, 1989.
Hardikar et al., "Coating of nanosize silver particles with silica", J. Colloid and Interface Science, 221:133-36, 2000.
Harrington et al., "Gene therapy for prostate cancer: current status and future prospects", J. Urology, 166:1220-33, 2001.
Hartl et al., "Ultrahigh-Resolution Optical Coherence Tomography Using Continuum Generation in an Air-Silica Microstructure Optical Fiber", Optics Letters, 26:608-610, 2001.
Hee et al., "Optical coherence tomography of the human retina", Arch. Ophthalmol. 113: 325-332, 1995.
Hiergeist et al., "Application of magnetite ferrofluids for hyperthermia", J. Magnetism and Magnetic Materials, 201:420-22, 1999.
Hirsch et al., "A Whole Blood Immunoassay Using Gold Nanoshells", Analytical Chemistry, 75:2377-2381, 2003.
Huang et al., "Optical Coherence Tomography", Science, 254: 1178-1181, 1991.
Jackson et al., "Silver Nanoshells:Variations in Morphologies and Optical Properties", J. Phys. Chem. B, 105:2743-46, 2001.
Jana et al., "Wet chemical synthesis of high aspect ratio cylindrical gold nanorods", J. Phys. Chem. B, 105:4065-67, 2001.
Jang et al,, "Visualization of Coronary Atherosclerotic Plaques in Patients Using Optical Coherence Tomography: Comparison With Intravascular Ultrasound", J. American College of Cardiology, 39:604-609, 2002.
Jensen et al., "Electrodynamics of noble metal nanoparticles and nanoparticle clusters", J. Cluster Science, 10:295-317, 1999.
Jin et al., "Photoinduced conversion of silver nanospheres to nanoprisms", Science, 294:1901-03, 2001.
Jordan et al., "Magnetic fluid hyperthermia (MFH): Cancer treatment with AC magnetic field induced excitation of biocompatible superparamagnetic nanoparticles", Magnetism and Magnetic Materials., 201:413-19, 1999.
Jue et al., "Addition of sulfhydryl groups to *Escherichia coli* ribosomes by protein modification with 2-iminothiolane (methyl 4-mercaptobutyrimidate)", Biochemistry, 17:5399-5406, 1978.

Kempka et al., "Binding, uptake, and transcytosis of ligands for mannose-specific receptors in rat liver: an electron microscopic study", Experimental Cell Research, 176, 38-48, 1988.
Keye et al., "Argon Laser Therapy of Endometriosis: A Review of 92 Consecutive Patients" Fertility and Sterility, 47:208-212, 1987.
Kim et al., "Hollow silica spheres of controlled size and porosity by sol-gel processing", J. Am. Ceram. Soc., 74:1987-1992, 1991.
Kim et al., "Photochemical synthesis of gold nanorods" J. Am. Chem. Soc., 124:14316-17, 2002.
Kim et al., "Self-Organization of Large Gold Nanoparticle Arrays", J. Am. Chem. Soc., 123:7955-56, 2001.
Kim et al., "Fabrication of hollow silica aerogel spheres by a droplet generation method and sol-gel processing" J. Vac. Sci., Technol. A., 7:1181-1184, 1989.
Kneipp at al., "Ultrasensitive Chemical Analysis by Raman Spectroscopy", Chem. Rev., 99:2957-75, 1999.
Kolb-Bachofen et al., "Electron microscopic evidence for an asialoglycoprotein receptor on Kupffer cells: localization of lectin-mediated endocytosis", Cell, 29:859-66, 1982.
Kolbeck, "The biomedical applications of protein microspheres", Ph.D. Doctoral Thesis, University of Illinois, Urbana-Champaign, title page and pp. 153, 159-160, 1999.
Korbelik et al., "Photofrin accumulation in malignant and host cell populations of various tumours", British Journal of Cancer, 73:506-513, 1996.
Langer "Drug delivery and targeting", Nature, 392:5-10, 1998.
Larson et al., "Water-Soluble Quantum Dots for Multiphoton Fluorescence Imaging in Vivo", Science, 300:1434-1436, 2003.
Lasic et al., "Liposomes revisited", Science, 267:1275-1276, 1995.
Lee et al., "Delivery of liposomes into cultured KB cells via folate receptor-mediated endocytosis", J. Biological Chemistry, 269:3198-3204, 1994.
Lee et al., "Engineered microsphere contrast agents for optical coherence tomography", Optics Letters, vol. 28, No. 17, pp. 1546-1548, 2003.
Lee et al., "Optical Characterization of Contrast Agents for Optical Coherence Tomography", Proceedings of SPIE, vol. 4967, pp. 129-134, 2003.
Leelarasamee et al., "A method for the preparation of polylactic acid microcapsules of controlled particle size and drug loading", J. Microencapsulation, 5:147-157, 1988.
Leitgeb et al., "Spectral measurement of absorption by spectroscopic frequency-domain optical coherence tomography", Optics Letters, 25:820-22, 2000.
Li et al., "Optical Coherence Tomography: Advanced Technology for the Endoscopic imaging of Barrett's Esophagus", Endoscopy, vol. 32, pp. 921-930, 2000.
Li et al., "Imaging Needle for Optical Coherence Tomography", Optics Letters, 25:1520-1522, 2000.
Li et al., "On the growth of highly ordered pores in anodized aluminum oxide", Chem. Mater., 10:2470-80, 1998.
Li et al., "Polycrystalline nanopore arrays with hexagonal ordering on aluminum", J. Vac. Sci. Technol. A, 17:1428-31, 1999.
Licha, "Contrast agents for optical imaging", Topics in Current Chemistry, 222:1-29, 2002.
Lin et al. "Measurement of tissue optical properties by the use of oblique-incidence optical fiber reflectometry", Applied Optics, 36:136-43, 1997.
Lin et al., "Intraocular Microsurgery with a Picosecond Nd:YAG Laser", Lasers in Surgery and Medicine, 15:44-53, 1994.
Liu et al., "In vivo measurement of oxygen concentration using sonochemically synthesized microspheres", Biophysical J., 67:896-901, 1994.
Liu et al., "A novel two-step silica-coating process for engineering magnetic nanocomposites", Chem. Mater., 10:3936-40, 1998.
Liz-Marzan et al., "Homogeneous silica coating of vitreophobic colloids", Chem. Commun., 731-32, 1996.
Lvov et al., "Nanoparticle/polyion assembly on microtemplates (lipid tubules and latex spheres)", Colloids and Surfaces B: Biointerfaces, 23:251-256, 2002.

Lvov et al., "Thin film nanofabrication via layer-by-layer adsorption of tubule halloysite, spherical silica, proteins and polycations", Colloids and Surfaces A: Physicohem. Eng. Aspects, 198-200:375-382, 2002.

Marks et al., Nonlinear interferometric vibrational imaging, E-print@arxiv.org/physics/0311071, URL http://www.arxiv.org/abs/physics/0311071, pp. 1-5, 2003.

Marks et al., "Study of an Ultrahigh-Numerical-Aperture Fiber Continuum Generation Source for Optical Coherence Tomography", Optics Letters, 27:2010-2012, 2002.

Marks et al., "Pulse shaping strategies for nonlinear interferometric vibrational imaging optimized for biomolecular imaging", Conference Proceeding: EMBC 2004: 26th Annual International Conference of the Engineering in Medicine and Biology Society (Sep. 1-5, 2004, San Francisco, CA), vol. 2, pp. 5300-5303 (accession No. 8255487).

Masuda et al., "Ordered metal nanohole arrays made by a two-step replication of honeycomb structures of anodic alumina", Science, 268:1466-68, 1995.

Mathias et al., "Tumor-selective radiopharmaceutical targeting via receptor-mediated endocytosis of Gallium-67-deferoxamine-folate", J. of Nuclear Medicine, 37:1003-1008, 1996.

McNamara III et al., "Sonoluminescence temperatures during multi-bubble cavitation", Nature, 401:772-775,1999.

Micali et al., "Separation of Scattering and Absorption Contributions in UV/Visible Spectra of Resonant Systems", Anal. Chem., 73:4958-63, 2001.

Minton et al., "The Laser in Surgery. A 23 Year Perspective.", American Journal of Surgery, 151:725-729, 1986.

Mock at al., "Composite plasmon resonant nanowires", Nano Letters, 2:465-69, 2002.

Mock et al., "Shape effects in plasmon resonance of individual colloidal silver nanoparticles", J. Chem. Phys., 116:6755-59, 2002.

Mohwald, "From Langmuir monolayers to nanocapsules", Colloids and Surfaces A: Physicochem. Eng. Aspects, 171:25-31, 2000.

Morgner et al., "Spectrosopic optical coherence tomography", Optics Letters, 25:111-13, 2000.

Nicewarner-Peña et al. "Submicrometer metallic barcodes", Science, 294:137-41, 2001.

Nielsch et al., "Self-ordering regimes of porous alumina: the 10% porosity rule", Nano Letters 2:677-80, 2002.

Novak et al., "Purification of molecularly bridged metallic nanoparticle arrays by centrifugation and size exclusion chromatography", Anal. Chem., 73:5758-61, 2001.

Oldenburg et al., "Light Scattering From Dipole and Quadrupole Nanoshell Antennas", Appl. Phys. Lett., 75:1063-65, 1999.

Pasternack et al., "Resonance Light Scattering: A New Technique for Studying Chromophore Aggregation", Science, 269:935-39, 1995.

Pathak et al., "Detection of squamous neoplasia by fluorescence imaging comparing porfimer sodium fluorescence to tissue autofluorescence in the hamster cheek-pouch model", American Journal of Surgery, 170:423-426, 1995.

Peters, All about Albumin, in Biochemistry, Genetics, and Medical Applications, (Academic Press, New York), p. 46, 1996.

Pinkerton et al., "Aerosolized fluorescent microspheres detected in the lung using confocal scanning laser microscopy", Microscopy Research and Technique, 26:437-443, 1993.

Pitris et al., "High-resolution imaging of gynecologic neoplasms using optical coherence tomography", Obstetrics & Gynecology, 93: 135-139, 1999.

Pitris et al., "Feasibility of optical coherence tomography for high-resolution imaging of human gastrointestinal tract malignancies", J. Gastroenterol., 35: 87-92, 2000.

Pollack et al., "Circumferential Argon Laser Photocoagulation for Prevention of Retinal Detachment", Eye, vol. 8, pp. 419-422, 1994.

Profio et al., "Transport of light in tissue in photodynamic therapy", Photochemistry and Photobiology, 46: 591-599, 1987.

Prudhomme et al., "Interstitial Diode Laser Hyperthermia in the Treatment of Subcutaneous Tumor", Lasers in Surgery and Medicine, 19:445-450, 1996.

Puliafito et al., "Imaging of macular disease with optical coherence tomography", Ophthalmology, 102: 217-229, 1995.

Puliafito et al., "Optical Coherence Tomography of Ocular Diseases", Slack Inc, Thorofare, N.J., pp. 3-34, 369-374, 1995.

Pusztay et al., "Encagement of Gold Nanoclusters in Crosslinked Resorcinarene Shells", Supramolecular Chemistry, 14:291-94, 2002.

Quaroni et al., "Preparation of Polymer-Coated Functionalized Silver Nanoparticles", J. Am. Chem. Soc., 121:10642-43, 1999.

Russell-Jones, "Use of vitamin $B_{12}$ conjugates to deliver protein drugs by the oral route", Critical Reviews in Therapuetic Drug Carrier Systems, vol. 15, No. 6, pp. 557-586, 1998.

Sadtler et al., "Spherical ensembles of gold nanoparticles on silica: electrostatic and size effects", Chem. Commun., 1604-05, 2002.

Sansdrap et al., "Influence of manufacturing parameters on the size characteristics and the release profiles of nifedipine from poly(DL-lactide-co-glycolide) microspheres", International Journal of Pharmaceutics, 98:157-164, 1993.

Schaefer et al., "Real-Time Digital Signal Processing-Based Optical Coherence Tomography and Doppler Optical Coherence Tomography", IEEE Transactions on Biomedical Engineering, vol. 51, No. 1, pp. 186-190, 2004.

Schaefer "Real-Time, Digital Signal Processing-Based Optical Coherence Tomography and Optical Doppler Tomography", Master Thesis, University of Illinois at Urbana-Champaign, 2001.

Schmitt et al., "Measurement of Optical Properties of Biological Tissues by Low-Coherence Reflectometry", Applied Optics., vol. 32, pp. 6032-6042, 1993.

Schmitt et al., "Subsurface Imaging of Living Skin with Optical Coherence Microscopy", Dermatology, vol. 191, pp. 93-98, 1995.

Schmitt et al., "Optical-coherence tomography of a dense tissue: statistics of attenuation and backscattering", Phys. Med. Biol., 39: 1705-1720, 1994.

Sergeev et al., "In vivo endoscopic OCT imaging of precancer and cancer states of human mucosa", Optics Express, 1: 432-440, 1997.

Sevick-Muraca et al., "Fluorescence-enhanced, near infrared diagnostic imaging with contrast agents", Current Opinion in Chemical Biology, Op. Chem. Biol., 6:642-50, 2002.

Shiga et al., "Preparation of Poly(D,L-lactide) and Copoly(lactide-glycolide) Microspheres of Uniform Size", J. Pharm. Pharmacol., 48:891-895, 1996.

Shipway et al., "Nanoparticle arrays on surfaces for electronic, optical, and sensor applications", ChemPhysChem., 1:18-52, 2000.

Sivak Jr. et al., "High-resolution endoscopic imaging of the GI tract using optical coherence tomography", Gastrointestinal Endoscopy, 51:474-479, 2000.

Slaga et al., "An animal model for oral cancer", J. National Cancer Institute Monographs, 13:55-60, 1992.

Sokolov et al., "Real-Time Vital Optical Imaging of Precancer Using Anti-Epidermal Growth Factor Receptor Antibodies Conjugated to Gold Nanoparticles", Cancer Research, 63:1999-2004, 2003.

Sönnichsen et al., "Drastic reduction of plasmon damping in gold nanorods", Physical Review Letters, vol. 88, No. 7:077402-1 to 077402-4, 2002.

Sönnichsen et al., "Spectroscopy of Single Metallic Nanoparticles Using Total Internal Reflection Microscopy", Appl. Phys. Lett., 77:2949-51, 2000.

Stavens et al., "Encapsulation of Neutral Gold Nanoclusters by Resorcinarenes", Langmuir, 15:8337-39, 1999.

Su et al., "Tumor characterization with dynamic contrast-enhanced MRI using MR contrast agents of various molecular weights", Magnetic Resonance in Medicine, 39:259-269, 1998.

Suslick et al., "Protein Microencapsulation of Nonaqueous Liquids", J. Am. Chem. Soc., 112:7807-7809, 1990.

Suslick et al., "Versatile sonochemical reaction vessels" in Experimental Organometallic Chemistry: A Practicum in Synthesis and Characterization, (A. Wayda, Darensburg MY, eds. ACS Symposium Series, Washington, D.C.), pp. 195-197, 1987.

Suslick, "Sonochemistry", Science, 247: 1439-1445, 1990.

Tanaka et al., "Direct visualization of colloidal gold-bound molecules and a cell-surface receptor by ultrahigh-resolution scanning electron microscopy", J. Microscopy, 161:455-61, 1991.

Tearney et al., "Optical Biopsy in Human Gastrointestinal Tissue Using Optical Coherence Tomography", American Journal of Gastroenterlogy, vol. 92, pp. 1800-1804, 1997.

Tearney et al., "Optical Biopsy in Human Urologic Tissue Using Optical Coherence Tomography", J. Urology, vol. 157, pp. 1915-1919, 1997.

Tearney et al., "Catheter-based optical imaging of a human coronary artery", Circulation, 94: 3013, 1996.

Tearney et al., "High-Speed Phase- and Group-Delay Scanning with a Grating-Based Phase Control Delay Line", Optics Letters, vol. 22, No. 23 :1811-1813, 1997.

Tearney et al., "In vivo endoscopic optical biopsy with optical coherence tomography", Science, 276: 2037-2039, 1997.

Tearney et al., "Rapid acquisition of in vivo biological images by use of optical coherence tomography", Optics Letters, 21: 1408-1410, 1996.

Tearney et al., "Scanning single-mode fiber optic catheter-endoscope for optical coherence tomography", Optics Letters, 21: pp. 543-545, 1996.

Templeton et al., "Monolayer-protected cluster molecules", Acc. Chem. Res., 33:27-36, 2000.

Timmerman et al., "Resorcinarenes" Tetrahedron, 52:2663-704, 1996.

Tkachenko et al., "Multifunctional Gold Nanoparticle-Peptide Complexes for Nuclear Targeting", J. Am. Chem. Soc., 125:4700-4701, 2003.

Toth et al., "Retinal effects of ultrashort laser pulses in the rabbit eye", Investigative Ophthalmology & Visual Science, 36:1910-17, 1995.

Toublan et al., "Magnetically-inducible optical contrast agents for optical coherence tomography", presented at the Optical Society of America Biomedical Topical Meeting, Miami, FL, Apr. 7-10, 2002.

Tripp et al., "Self-assembly of cobalt nanoparticle rings", J. Am. Chem. Soc., 124:7914-15, 2002.

Turkevich et al., "A Study of the Nucleation and Growth Processes in the Synthesis of Colloidal Gold", Faraday Soc., 11:55-75, 1951.

Tuting, "The immunology of cutaneous DNA immunization", Current Opinion in Molecular Therapeutics, vol. 1, No. 2, pp. 216-225, 1999.

Ung et al., "Controlled method for silica coating of silver colloids. Influence of coating on the rate of chemical reactions", Langmuir, 14:3740-48, 1998.

van der Laan et al., "In vitro activity of novel antifolates against human squamous carcinoma cell lines of the head and neck with inherent resistance to methotrexate", Int. J. Cancer, 51:909-914, 1992.

Van Der Smissen et al., "Ligand-induced clustering of asialoglycoprotein receptors on rat hepatocytes at 4° C", European J. of Cell Biology, 60:122-30, 1993.

Van Der Smissen et al., "Quantitative analysis of clustering on biological membranes: methodology and application to ligand-induced asialoglycoprotein receptor redistribution on rat hepatocytes", European J. of Cell Biology, 69:45-54, 1996.

van der Zande et al., "Colloidal dispersions of gold rods: synthesis and optical properties", Langmuir, 16:451-58, 2000.

Violante et al., "Improved detectability of VX2 carcinoma in the rabbit liver with contrast enhancement in computed tomography", Radiology, 134:237-239, 1980.

Vitkin et al., "Optical and thermal characterization of natural (*Sepia officinalis*) melanin", Photochemistry and Photobiology, 59:455-62, 1994.

Vo-Dinh, "Surface-Enhanced Raman Spectroscopy Using Metallic Nanostructures", Trends in Analytical Chemistry, 17:557-82, 1998.

Wang et al., "Semiconductor quantum dot-labeled microsphere bioconjugates prepared by stepwise self-assembly", Nano Lett., 2:857-861, 2002.

Wang et al., "Use of a Laser Beam with an Oblique Angle of Incidence to Measure the Reduced Scattering Coefficient of a Turbid Medium", Applied Optics, 34:2362-2366, 1995.

Webb et al., "Sonochemically produced fluorocarbon microspheres: a new class of magnetic resonance imaging agent", J. Magnetic Resonance Imaging, 6:675-683, 1996.

Wei et al., "Resorcinarene-encapsulated nanoparticles: building blocks for self-assembled nanostructures", J. Inclusion Phenomenal Macrocyclic Chemistry, 41, 83-86, 2001.

Wei et al., "Synthesis and Characterization of Resorcinarene-Encapsulated Nanoparticles", Mater. Res. Soc., Symp. Proc. Ser., 581:59-63, 1999.

Wei et al., "Tunable Surface-Enhanced Raman Scattering from Large Gold Nanoparticle Arrays", ChemPhysChem., 2:743-45, 2001.

Wong et al., "Sonochemically produced hemoglobin microbubbles", Mat. Res. Soc. Symp. Proc., 372:89-94, 1995.

Xu et al., "Electromagnetic Contributions to Single-Molecule Sensitivity in Surface-Enhanced Raman Scattering", Physical Review E, 62:4318-24, 2000.

Yazdanfar et al., "High Resolution Imaging of in vivo Cardiac Dynamics Using Color Doppler Optical Coherence Tomography", Optics Express, vol. 1, pp. 424-431, 1997.

Yguerabide et al., "Light-scattering submicroscopic particles as highly fluorescent analogs and their use as tracer labels in clinical and biological applications", Analytical Biochemistry, 262:137-56, 1998.

Yu et al., "Gold nanorods: electrochemical synthesis and optical properties", J. Phys. Chem. B, 101:6661-64, 1997.

Zaheer et al., "In vivo near-infrared fluorescence imaging of osteoblastic activity", Nature Biotechnology, 19:1148-54, 2001.

Marks et al., "Interferometric differentiation between resonant Coherent Anti-Stokes Raman Scattering and nonresonant four-wave-mixing processes", arXiv:physics/0403007, pp. 1-8, 2004.

Vinegoni et al., "Nonlinear optical contrast enhancement for optical coherence tomography", Optics Express, vol. 12, No. 2, p. 331-341, 2004.

Kee et al., "Simple approach to one-laser, broadband coherent anti-Stokes Raman scattering microscopy", Optics Letters, vol. 29, No. 23, p. 2701-2703, 2004.

Kano et al., "Vibrationally resonant imaging of a single living cell by supercontinuum-based multiplex coherent anti-Stokes Raman scattering microspectroscopy", Optics Express, vol. 13, Issue 4, pp. 1322-1327, 2005.

Gao et al., "Formulation, Characterization, and Sensing Applications of Transparent Poly(vinyl alcohol)-Polyelectrolyte Blends", Chem. Mater., 10, pp. 2481-2489, 1998.

Marks et al., Molecular Species Sensitive Optical Coherence Tomography Using Coherent Anti-Stokes Raman Scattering Spectroscopy, Coherence Domain Optical Methods and Optical Coherence Tomography in Biomedicine VII, Proceedings of SPIE, vol. 4956, pp. 9-13, 2003.

Bredfeldt et al., "Non-linear interferometric vibrational imaging", Conference on Lasers and Electro-optics, CLEO '03, pp. 309-311, 2003.

Vinegoni et al., "Nonlinear optical contrast enhancement for optical coherence tomography", http://www.arxiv.org/abs/physics/0312114, 13 pages (2003).

Zumbusch et al., "Three-dimensional vibrational imaging by coherent anti-Stokes Raman scattering", Phys. Rev. Lett., 82(20), pp. 4142-4145, 1999.

Cheng et al., "An epi-detected coherent anti-Stokes Raman scattering (E-CARS) microscope with high spectral resolution and high sensitivity", J. Phys. Chem, 105(7), pp. 1277-1280, 2001.

Hashimoto et al., "Molecular vibration imaging in the fingerprint region by use of coherent anti-Stokes Raman scattering microscopy with a collinear configuration", Opt. Lett., 25(24), pp. 1768-1770, 2000.

Volkmer et al., "Vibrational imaging with high sensitivity via epidected coherent anti-Stokes Raman scattering microscopy", Phys. Rev. Lett., 87(2):023901-1-4, 2001.

Schmitt, J.M. et al., "Optical-coherence tomography of a dense tissue: statistics of attenuation and backscattering", Phys. Med. Biol., vol. 39, pp. 1705-1720, (1994).

Tearney, G.J. et al., "In vivo endoscopic optical biopsy with optical coherence tomography", Science, vol. 276, pp. 2037-2039, (1997).

Huang, D. et al., "Optical Coherence Tomography", Science, 254, 5035, pp. 1178-1181, (1991).

Fercher, A.F. et al., "Optical Coherence Tomography—principles and applications", Institute of Physics Publishing, Reports on Progress in Physics, 66, pp. 239-303, (2003).

Boppart, S.A. et al., "Optical probes and techniques for molecular contrast enhancement in coherence imaging", J. Biomedical Optics, 10(4), pp. 041208-1 thru 041208-14, (2005).
Oldenburg, A.L. et al., "Imaging magnetically labeled cells with magnetomotive optical coherence tomography", Optics Letters, 30, 7, pp. 747-749, (2005).
Oldenburg, A.L. et al., "Selective OCT imaging of cells using magnetically-modulated optical contrast agents", in Proceedings of the Conference on Lasers and Electro-Optics, pp. 405-4-6, (2003).
Kopelman, R. et al., "Multifunctional nanoparticle platforms for in vivo MRI enhancement and photodynamic therapy of a rat brain cancer", J. Magnetism and Magnetic Materials, 293, pp. 404-410, (2005).
Romanus, E. et al., "Magnetic nanoparticle relaxation measurement as a novel tool for in vivo diagnostics", J. Magnetism and Magnetic Materials, 252, pp. 387-389, (2002).
Oldenburg, A.L. et al., "Magnetomotive contrast for in vivo optical coherence tomography", Optics Express, 13, 17, pp. 6597-6614, (2005).
Oh, J. et al., "Detection of magnetic nanoparticles in tissue using magneto-motive ultrasound", Nanotechnology, 17, pp. 4183-4190, (2006).
Joo, C. et al., "Spectral-domain optical coherence phase microscopy for quantitative phase-contrast imaging", Optics Letters, 30, 16, pp. 2131-2133, (2005).
Choma, M.A. et al., "Spectral-domain phase microscopy", Optics Letters, 30, 10, pp. 1162-1164, (2005).
Choma, M.A. et al., "Doppler flow imaging of cytoplasmic streaming using spectral domain phase microscopy", J. Biomedical Optics 11(2), pp. 024014-1 thru 024014-8, (2006).
Sticker, M. et al., "En face imaging of single cell layers by differential phase-contrast optical coherence microscopy", Optics Letters, 27, 13, pp. 1126-1128, (2002).
Sarunic, M.V. et al., "Full-field swept-source phase microscopy", Optics Letters, 31, 10, pp. 1462-1464, (2006).
De la Torre-Ibarra, M.H. et al., "Double-shot depth-resolved displacement field measurement using phase-contrast spectral optical coherence tomography", Optics Express, 14, 21, pp. 9643-9656, (2006).
Vakoc, B.J. et al., "Phase-resolved optical frequency domain imaging", Optics Express, 13, 14, pp. 5483-5493, (2005).
Pedersen, C.J. et al., "Phase-referenced Doppler optical coherence tomography in scattering media", Optics Letters, 30, 16, pp. 2125-2127, (2005).
Ren, H. et al., "Imaging and quantifying transverse flow velocity with the Doppler bandwidth in a phase-resolved functional optical coherence tomography", Optics Letters, 27, 6, pp. 409-411, (2002).
Zhao, Y. et al., "Doppler standard deviation imaging for clinical monitoring of in vivo human skin blood flow", Optics Letters, 25, 18, pp. 1358-1360, (2000).
Ren, H. et al., "Phase-resolved functional optical coherence tomography: simultaneous imaging of in situ tissue structure, blood flow velocity, standard deviation, birefringence, and Stokes vectors in human skin", Optics Letters, 27, 19, pp. 1702-1704, (2002).
Ding, Z. et al., "Real-time phase-resolved optical coherence tomography and optical Doppler tomography", Optics Express, 10, 5, pp. 236-244, (2002).
White, B.R. et al., "In vivo dynamic human retinal blood flow imaging using ultra-high-speed spectral domain optical Doppler tomography", Optics Express, 11, 25, pp. 3490-3496, (2003).
Ren, H. et al., "Real-time in vivo blood-flow imaging by moving-scatterer-sensitive spectral-domain optical Doppler tomography", Optics Letters, 31, 7, pp. 927-929, (2006).
Fang-Yen, C. et al., "Noncontact measurement of nerve displacement during action potential with a dual-beam low-coherence interferometer", Optics Letters, 29, 17, pp. 2028-2030, (2004).
Choma, M.A. et al., "Sensitivity advantage of swept source and Fourier domain optical coherence tomography", Optics Express, vol. 11, No. 18, pp. 2183-2189, (2003).
Leitgeb, R. et al., "Performance of fourier domain vs. time domain optical coherence tomography", Optics Express, 11, 8, pp. 889-894, (2003).

Leitgeb, R.A. et al., "Ultrahigh resolution Fourier domain optical coherence tomography", Optics Express, 12, 10, pp. 2156-2165, (2004).
De Boer, J.F. et al., "Improved signal-to-noise ratio in spectral-domain compared with time-domain optical coherence tomography", Optics Letters, 28, 21, pp. 2067-2069, (2003).
Ralston, T.S. et al., "Phase Stability Technique for Inverse Scattering in Optical Coherence Tomography", International Symposium on Biomedical Imaging, pp. 578-581, (2006).
Yang, C. "Molecular contrast optical coherence tomography: A review", Photochemistry and Photobiology 81, pp. 215-237, (2005).
Kim, J. et al., "Hemoglobin contrast in magnetomotive optical Doppler tomography", Optics Letters, 31, 6, pp. 778-780, (2006).
Oh, J. et al., "Magneto-motive detection of tissue-based macrophages by differential phase optical coherence tomography", Lasers in Surgery and Medicine, 39, pp. 266-272, (2007).
Crecea, V. et al., "Phase-resolved spectral-domain magnetomotive optical coherence tomography", Proc. of SPIE, 6429, pp. 64291X-1 thru 64291X-10, (2007).
Oldenburg, A.L. et al., "Magnetic contrast agents for optical coherence tomography", Proc. of SPIE, 5316, pp. 91-92, (2004).
Oldenburg, A.L. et al., "High-resolution in vivo nanoparticle imaigng using magnetomotive optical coherence tomography", Proc. of SPIE, 6097, pp. 609702-1 thru 609702-11, (2006).
Schmitt, J.M. "OCT elastography: imaging microscopic deformation and strain of tissue", Optics Express, 3, 6, pp. 199-211, (1998).
Gleich, B. et al., "Tomographic imaging using the nonlinear response of magnetic particles", Nature, 435, pp. 1214-1217, (2005).
Anker, J.N. et al., "Magnetically modulated optical nanoprobes", Applied Physics Letters, 82, 7, pp. 1102-1104, (2003).
Harisinghani, M.G. et al., "Noninvasive Detection of Clinically Occult Lymph-Node Metastases in Prostate Cancer", New England J. of Medicine, 348, 25, pp. 2491-2499, (2003).
Arbab, A.S. et al., "In vivo trafficking and targeted delivery of magnetically labeled stem cells", Human Gene Therapy, 15, pp. 351-360, (2004).
Alexiou, C. et al., "Locoregional cancer treatment with magnetic drug targeting", Cancer Research, 60, pp. 6641-6648, (2000).
Winter, P.M. et al., "Molecular imaging of angiogenesis in early-stage atherosclerosis with integrin-targeted nanoparticles", Circulation, 108, pp. 2270-2274, (2003).
Mornet S. et al., "Magnetic nanoparticle design for medical diagnosis and therapy", J. of Materials Chemistry, 14, pp. 2161-2175, (2004).
Kim, J. et al., "Imaging nanoparticle flow using magneto-motive optical Doppler tomography", Nanotechnology, 18, 035504, pp. 1-6, (2007).
Oldenburg, A.L. et al., "Spectral-Domain Magnetomotive OCT Imaging of Magnetic Nanoparticle Biodistribution", Proc. of SPIE, vol. 6847, pp. 684719-1 thru 684719-8, (2008).
Oldenburg, A.L. et al., "Phase-resolved magnetomotive OCT for imaging nanomolar concentrations of magnetic nanoparticles in tissues", Optics Express, 16(15), pp. 11525-11539, (2008).
Oldenburg, A.L. et al., "Optical micro-scale mapping of dynamic biomechanical tissue properties", Optics Express, 16(15), pp. 11052-11065, (2008).
Oldenburg, A.L. et al., "Spectroscopic optical coherence tomography and microscopy", IEEE Journal of Selected Topics in Quantum Electronics, special issue on Biophotonics, 13(6), pp. 1629-1640, (2007).
Zysk, A.M. et al., "Optical coherence tomography: A review of clinical development from bench to bedside", Special section on optical diagnostic imaging from bench to bedside, Journal of Biomedical Optics, 12(5), pp. 051403-1 thru 051403-20, (2007).
Tan, W. et al., "Optical coherence tomography of cell dynamics in three-dimensional tissue models", Optics Express, 14(16), pp. 7159-7171, (2006).
Oldenburg, A.L. et al., "Plasmon-resonant gold nanorods as law backscattering albedo contrast agents for optical coherence tomography", Optics Express, vol. 14, No. 15, pp. 6724-6738, (2006).
Senin, A.A. et al., "Molecular dissociation observed with an atomic wavepacket and parametric four-wave mixing", Chemical Physics Letters, 381, pp. 53-59, (2003).

Oldenburg, A.L. et al., "Fast Fourier-domain delay line for in vivo optical coherence tomography with a polygonal scanner", Applied Optics, 42(22), pp. 4606-4611, (2003).

Marks, D.L. et al., "Autofocus algorithm for dispersion correction in optical coherence tomography", Applied Optics, 42(16), pp. 3038-3046, (2003).

Marks, D.L. et al., "Digital algorithm for dispersion correction in optical coherence tomography for homogeneous and stratified media", Applied Optics, vol. 42, No. 2, pp. 204-217, (2003).

Oldenburg, A.L. et al., "Vibrational wave packets in the $^{B1\Pi}_u$ and $D^{1\Sigma}_u{}^+$ states of Cs2: Determination of improved Cs2+(X) and Cs2(B) spectroscopic constants", Journal of Chemical Physics, 113(24), pp. 11009-11018, (2000).

Oldenburg, A.L. et al., "Optically pinpointing magnetic nanoparticles within biological tissue", Optics & Photonics News, 17(12), p. 24, (2006).

Nguyen, F.T. et al., "Magnetic protein microspheres as dynamic contrast agents for magnetomotive optical coherence tomography", Proc. of SPIE, 6867, pp. 68670F-1 thru 68670F-11, (2008).

Oldenburg, A.L. et al., "Plasmon-resonant gold nanorods provide spectroscopic OCT contrast in excised human breast tumors", Proc. of SPIE, 6867, pp. 68670E-1 thru 68670E-10, (2008).

Oldenburg, A.L. et al., "Spectral-domain magnetomotive OCT imaging of magnetic nanoparticle biodistribution", Proc. of SPIE, 6847, pp. 684719-1 thru 684719-11, (2008).

Liang, X. et al., "Modeling and measurement of tissue elastic moduli using optical coherence elastography", Proc. of SPIE, 6858, pp. 685803-1 thru 685803-8, (2008).

Oldenburg, A.L. et al., "Backscattering albedo contrast in OCT using plasmon-resonant gold nanorods", Proc. of SPIE, 6429, pp. 64291Z-1 thru 6429Z-8, (2007).

Oldenburg, A.L. et al., "Characterization of plasmon-resonant gold nanorods as near-infrared optical contrast agents investigated using a double-integrating sphere system", Proc. of SPIE, 5703, pp. 50-60, (2005).

Oldenburg, A.L. et al., "Magnetic contrast agents for optical coherence tomography." Proc. of SPIE, 5316, pp. 91-98, (2004).

Oldenburg, A.L. et al., "Optical manipulation of silicon microparticles in biological environments", Proc. of SPIE, 4962, pp. 249-255, (2003).

Oldenburg, A.L., "Wavepacket dynamics and time-domain spectroscopy in atomic rubidium", Quantum Electronics and Laser Science Conference 1999, Technical Digest, Thursday Morning, pp. 176-177, (1999).

Swanson, E.A. et al., "In vivo retinal imaging by optical coherence tomography", Optics Letters, 18, 21, pp. 1864-1866, (1993).

American Academy of Pediatrics, Clinical Practice Guideline, "Otitis Media with Effusion", Pediatrics, 113, 5, pp. 1412-1429, (2004).

Pitris, C. et al., "High-resolution imaging of the middle ear with optical coherence tomography: A feasibility study," Arch Otolaryngol Head Neck Surg., 127, pp. 637-642, (2001).

Hall-Stoodley, L. et al., "Direct detection of bacterial biofilms on the middle-ear mucosa of children with chronic otitis media," JAMA, 296, 2, pp. 202-211, (2006).

Xi, C. et al., "High-resolution three-dimensional imaging of biofilm development using optical coherence tomography," J. Biomed. Opt., 11(3), pp. 034001-1 thru 034001-6, (2006).

Leitgeb, R. et al., "Performance of Fourier domain vs. time domain optical coherence tomography," Optics Express, 11, 8, 889-894, (2003).

Ralston, T.S. et al., "Interferometric synthetic aperture microscopy", Nature Physics, 3, pp. 129-134, (2007).

Ralston, T.S. et al., "Inverse Scattering for Optical Coherence Tomography", J. Opt. Soc. Am. A, 23, 5, pp. 1027-1037, (2006).

Sitter, D.N. et al., "Three-dimensional Imaging: a Space invariant Model for Space Variant Systems", Applied Optics, 29, 26, pp. 3789-3794, (1990).

Choma, M.A. et al., "Sensitivity advantage of swept source and Fourier domain optical coherence tomography", Optics Express, 11, 18, pp. 2183-2189, (2003).

Ralston, T.S. et al., "Phase Stability Technique for Inverse Scattering in Optical Coherence Tomography", Biomedical Imaging: Nano to Macro, 3rd IEEE International Symposium on Biomedical Imaging, pp. 578-581, (2006).

Costerton, J.W. et al., "Bacterial biofilms: a common cause of persistent infections", Science, 284, pp. 1318-1322, (1999).

Donlan, R.M., "Biofilms and device-associated infections", Emerging Infectious Diseases, 7, 2, pp. 277-281, (2001).

Donlan, R.M. "Biofilms: microbial life on surfaces", Emerging Infectious Diseases, 8, 9, pp. 881-890, (2002).

Fux, C.A. et al., "Survival strategies of infectious biofilms", Trends in Microbiology, 13, 1, pp. 34-40, (2005).

Takata, G.S. et al., "Evidence Assessment of the Accuracy of Methods of Diagnosing Middle Ear Effusion in Children With Otitis Media With Effusion", Pediatrics, 112, 6, pp. 1379-1387, (2003).

Reed, W.A. et al., "Gradient-index fiber-optic microprobes for minimally invasive in vivo low-coherence interferometry," Optics Letters, 27, 20, pp. 1794-1796, (2002).

Vinegoni, C. et al., "Integrated structural and functional optical imaging combining spectral-domain optical coherence and multiphoton microscopy", Applied Physics Letters, 88, pp. 053901-1 thru 053901-3, (2006).

Crecea, V., "Phase-resolved spectral-domain magnetomotive optical coherence tomography for microscopic analysis of biomechanical properties", Preliminary Examination, pp. 1-15, (2007).

Xu, C. et al., "Near-infrared dyes as contrast-enhancing agents for spectroscopic optical coherence tomography", Optics Letters, vol. 29, No. 14, pp. 1657-1649, (2004).

Nguyen, F.T. et al., "Portable Real-Time Optical Coherence Tomography System for Intraoperative Imaging and Staging of Breast Cancer", Proc. Of SPIE, vol. 6430, pp. 64300H-1 thru 64300H1-10, (2007).

Zysk, A.M. et al., "Needle-probe system for the measurement of tissue refractive index", Proc. Of SPIE, vol. 6430, pp. 64300O-1-64300O-8, (2007).

Pasquesi, J.J. et al., "Detection of ultrastructural changes in genetically-altered and exercised skeletal muscle using PS-OCT", Proc. Of SPIE, vol. 6079, pp. 607926-1-607926-7, (2006).

Xu, C. et al., "Spectroscopic spectral-domain optical coherence microscopy", Optics Letters, vol. 31, No. 8, pp. 1079-1081, (2006).

Jones, G.W. et al., "High-spectral-resolution coherent anti-stokes raman scattering with interferometrically detected broadband chirped pulses", Optics Letters, vol. 31, No. 10, pp. 1543-1545, (2006).

Boppart, S.A., "Advances in contrast enhancement for optical coherence tomography", Proceedings of the 28th IEEE EMBS Annual International Conference New York City, USA, pp. 121-124, Aug. 30-Sep. 3, 2006.

Marks, D.L. et al., "High numerical aperture full-field optical coherence tomography with space-invariant resolution without scanning the focus", Proc. Of SPIE, vol. 6429, pp. 64291R1-64291R-9, (2007).

Luo, W. et al., "Three-dimensional optical coherence tomography of the embryonic murine cardiovascular system", Journal of Biomedical Optics, vol. 11(2), pp. 021014-1-021014-8, (2006).

Marks, D.L. et al., "Inverse scattering for frequency-scanned full-field optical coherence tomography", Journal of the Optical Society of America A, vol. 24, No. 4, pp. 1034-1041, (2007).

Ralston, T.S. et al., "Inverse scattering for high-resolution interferometric microscopy", Optics Letters, vol. 31, No. 24, pp. 3585-3587, (2006).

Ralston, T.S. et al., "Demonstration of inverse scattering in optical coherence tomography", Proc. Of SPIE, vol. 6079, pp. 60791T-1-60791T-9, (2006).

Marks, D.L. et al., "Inverse scattering for rotationally scanned optical coherence tomography", J. Opt. Soc. Am. A, vol. 23, No. 10, pp. 2433-2439, (2006).

Zysk, A.M. et al., "Needle-based reflection refractometry of scattering samples using coherence-gated detection", Optics Express, vol. 15, No. 8, pp. 4787-4794, (2007).

Pasquesi, J.J. et al., "In vivo detection of exercise-induced ultrastructural changes in genetically-altered murine skeletal muscle using polarization-sensitive optical coherence tomography", Optics Express, vol. 14, No. 4, pp. 1547-1556, (2006).
Ko, H.J. et al., "Optical coherence elastography of engineered and developing tissue", Tissue Engineering, vol. 12, No. 1, pp. 63-73, (2006).
Zhu, C. et al., "Use of a multiseparation fiber optic probe for the optical diagnosis of breast cancer", Journal of Biomedical Optics, vol. 10(2), p. 024032-1-024032-13, (2005).
Bigio, I.J. et al., "Diagnosis of breast cancer using elastic-scattering spectroscopy: preliminary clinical results", Journal of Biomedical Optics, vol. 5, No. 2, pp. 221-228, (2000).
Bitar, R.A. et al., "Biochemical analysis of human breast tissues using Fourier-transform Raman spectroscopy", Journal of Biomedical Optics, vol. 11(5), p. 054001-1-054001-8, (2006).
Demos, S.G. et al., "Investigation of near-infrared autofluorescence imaging for the detection of breast cancer", IEEE Journal of Selected Topics in Quantum Electronics, vol. 11, No. 4, pp. 791-798, (2005).
Demos, S.G. et al., "Advances in optical spectroscopy and imaging of breast lesions", Journal of Mammary Gland Biology and Neoplasia, vol. 11, pp. 165-181, (2006).
Fournier, L.S. et al., "In-vivo NIR autofluorescence imaging of rat mammary tumors", Optics Express, vol. 14, No. 15, pp. 6713-6723, (2006).
Frank, C.J. et al., "Characterization of human breast biopsy specimens with near-IR Raman-spectroscopy", Analytical Chemistry, vol. 66, No. 3, pp. 319-326, (1994).
Gupta, P.K. et al., "Breast cancer diagnosis using N2 laser excited autofluorescence spectroscopy", Lasers in Surgery and Medicine, vol. 21, pp. 417-422, (1997).
Haka, A.S. et al., "Identifying microcalcifications in benign and malignant breast lesions by probing differences in their chemical composition using Raman spectroscopy", Cancer Research, vol. 62, pp. 5375-5380, (2002).
Haka, A.S. et al., "Diagnosing breast cancer by using Raman spectroscopy", Proceedings of the National Academy of Sciences of the United States of America, vol. 102, No. 35, pp. 12371-12376, (2005).
Haka, A.S. et al., "In vivo margin assessment during partial mastectomy breast surgery using Raman spectroscopy", Cancer Research, vol. 66, pp. 3317-3322, (2006).
Iftimia, N.V. et al., "A portable, low coherence interferometry based instrument for fine needle aspiration biopsy guidance", Review of Scientific Instruments, vol. 76, p. 064301-1-064301-6, (2005).
Lenkinski, R.E. et al., "Near-infrared fluorescence imaging of microcalcification in an animal model of breast cancer", Academic Radiology, vol. 10, pp. 1159-1164, (2003).
Manoharan, R. et al., "Raman spectroscopy and fluorescence photon migration for breast cancer diagnosis and imaging", Photochemistry and Photobiology, vol. 67(1), pp. 15-22, (1998).
Motz, J.T. et al., "Optical fiber probe for biomedical Raman spectroscopy", Applied Optics, vol. 43, No. 3, pp. 542-554, (2004).
Palmer, G.M. et al., "Diagnosis of breast cancer using optical spectroscopy", Medical Laser Application, vol. 18, pp. 233-248, (2003).
Palmer, G.M. et al., "Comparison of multiexcitation fluorescence and diffuse reflectance spectroscopy for the diagnosis of breast cancer", IEEE Transactions on Biomedical Engineering, vol. 50, No. 11, pp. 1233-1242, (2003).
Peters, V.G. et al., "Optical properties of normal and diseased human breast tissues in the visible and near infrared", Physics in Medicine and Biology, vol. 35, No. 9, pp. 1317-1334, (1990).
Redd, D.C.B. et al., "Raman spectroscopic characterization of human breast tissues: Implications for breast cancer diagnosis", Applied Spectroscopy, vol. 47, No. 6, pp. 787-791, (1993).

Shafer-Peltier, A.S. et al., "Raman microspectroscopic model of human breast tissue: implications for breast cancer diagnosis in vivo", Journal of Raman Spectroscopy, vol. 33, pp. 552-563, (2002).
Shah, N. et al., "Noninvasive functional optical spectroscopy of human breast tissue", Proceedings of the National Academy of Sciences of the United States of America, vol. 98, No. 8, pp. 4420-4425, (2001).
Shetty, G. et al., "Raman spectroscopy: elucidation of biochemical changes in carcinogenesis of oesophagus", British Journal of Cancer, vol. 94, pp. 1460-1464, (2006).
Yang, Y. et al., "Fundamental differences of excitation spectrum between malignant and benign breast tissues", Photochemistry and Photobiology, vol. 66(4), pp. 518-522, (1997).
Zysk, A.M. et al., "Optical coherence tomography: a review of clinical development from bench to bedside", J. Biomedical Optics, 12(5), pp. 051403-1 thru 051403-21, (2007).
Choi, J.H. et al., "Multimodal biomedical imaging with asymmetric single-walled carbon nanotube/iron oxide nanoparticle complexes", Nano Letters, vol. 7, No. 4, pp. 861-867, (2007).
Zysk, A.M. et al., Comment on "In vivo cancer diagnosis with optical spectroscopy and acoustically induced blood stasis using a murine Mca35 model", Medical Physics, vol. 34, Issue 3, p. 1130, (2007).
Boppart, M.D. et al., "$\alpha 7 \beta 1$—Integrin regulates mechanotransduction and prevents skeletal muscle injury", American Journal of Physiology: Cell Physiology, vol. 290, Issue 6, pp. C1660-C1665, (2006).
Toublan, F.J-J. et al., "Tumor targeting by surface-modified protein microspheres", Journal of the American Chemical Society, vol. 128, Issue 11, pp. 3472-3473, (2006).
Vinegoni, C. et al., "Integrated structural and functional optical imaging combining spectral-domain optical coherence and multiphoton microscopy", Applied Physics Letters, vol. 88, Issue 5, pp. 053901-1 thru 053901-3, (2006).
Vinegoni, C. et al., "Multi-modality imaging of structure and function combining spectral-domain optical coherence and multiphoton microscopy", Proc. of SPIE, vol. 6079, pp. 60791D-1 thru 60791D-8, (2006).
Boppart, S.A. et al., "Real-time optical biopsy and analysis of breast cancer using clinical optical coherence tomography", Journal of Clinical Oncology, Abstract presentation from the 2007 ASCO Annual Meeting Proceedings Part 1, vol. 25, No. 18S, (2007).
American Cancer Society, "2007 Cancer facts & figures", 56 pages, (2007).
Boppart, S.A. et al., "Optical coherence tomography: feasibility for basic research and image-guided surgery of breast cancer", Breast Cancer Research and Treatment, vol. 84, pp. 85-97, (2004).
Berg, W.A. et al., "Diagnostic accuracy of mammography, clinical examination, US, and MR imaging in preoperative assessment of breast cancer", Radiology, vol. 233, pp. 830-849, (2004).
Kawasaki, M., et al., "Diagnostic accuracy of optical coherence tomography and integrated backscatter intravascular ultrasound images for tissue characterization of human coronary plaques", Journal of the American College of Cardiology, vol. 48, No. 1, pp. 81-88, (2006).
Oldenburg, A.L. et al., "Molecular OCT contrast enhancement and imaging", Optical Coherence Tomography: Technology and Applications, Ch. 24, (2008).
Oldenburg, A.L. et al., "Optical coherence tomography", McGraw-Hill Encyclopedia of Science & Technology, (2005).
Oldenburg, A.L et al., "Imaging gold nanorods in excised human breast carcinoma by spectroscopic optical coherence tomography", Journal of Materials Chemistry, (2009).

* cited by examiner

CONTRAST ENHANCED SPECTROSCOPIC OPTICAL COHERENCE TOMOGRAPHY

REFERENCE TO RELATED APPLICATIONS

This application claims the benefit of U.S. Provisional Application No. 60/672,205 entitled "Contrast Enhanced Spectroscopic Optical Coherence Tomography" filed Apr. 15, 2005, which is incorporated by reference in its entirety.

FEDERALLY SPONSORED RESEARCH OR DEVELOPMENT

The subject matter of this application may have been funded in part under a research grants from the National Aeronautics and Space Administration (NASA), under Contract Number NAS2-02057. The U.S. Government may have rights in this invention.

BACKGROUND

Optical coherence tomography (OCT) is a high-resolution medical and biological imaging technology. OCT has been used in ophthalmology for high-resolution tomographic imaging of the retina and anterior eye. Recently, the technique has been applied for imaging a wide range of nontransparent tissues to investigate applications in tissues studies and medical applications in gastroenterology, urology, and neurosurgery. OCT detects the reflections of low-coherence light, and cross-sectional imaging may be performed by measuring the backscattered intensity of light from structures in tissue. This imaging technique is attractive for medical imaging because it permits the imaging of tissue microstructure in situ. In situ imaging with OCT may provide micron-scale imaging resolution without the need for excision and histological processing.

Spectroscopic optical coherence tomography (SOCT) is an extension of OCT that can provide depth resolution and can differentiate between different types of tissue. In addition to the normal OCT measurement of the intensity of light backscattered from the sample, SOCT measures the spectral absorption and reflectance data from the tissue. Tissue structure can be resolved based on local optical densities, ignoring the frequency dependent changes. SOCT resolves both the amplitude, which contains the density information, and the frequency, which contains the spectroscopic molecular composition information.

Contrast agents may be used to improve the resolution of images obtained from an imaging technique, including OCT. Conventional contrast agents serve to increase the intensity of backscattered light. For example, air-filled micro-bubbles and engineering microspheres may be introduced into tissue to increase the back-scattering from tissue. In another example, a molecular contrast agent can be generated using a pump-probe technique to change the absorption.

A method to increase the types of tissue that may be resolved with SOCT methods would be beneficial. For example, substances such as melanin and hemoglobin exhibit strong selective absorption signature, and may be directly resolved by conventional SOCT. However, these substances are common in tissue and often may not be used to discriminate tissue types. It would be desirable to provide contrast agents that could improve and expand the application of SOCT. It would also be desirable to extract additional information from tissue samples regarding the structure and the composition of the tissue.

SUMMARY

In one aspect, the invention provides a method of forming an image of a sample.

In another aspect, the invention provides a method of performing SOCT on a sample.

In yet another aspect, the invention provides a method of selecting a contrast agent.

In yet another aspect, the invention provides a method of selecting a combination of an absorbing agent and a scattering agent.

In yet another aspect, the invention provides a method of performing SOCT on a sample comprising at least one absorbing agent and at least one scattering agent.

In yet another aspect, the invention provides a method of enhancing the contrast of an image of a sample.

In yet another aspect, the invention provides a method of separately quantifying the contributions to SOCT data of at least one absorbing agent and at least one scattering agent in a sample.

In yet another aspect, the invention provides a method of forming an image of tissue that includes selecting at least one contrast agent, delivering the at least one contrast agent to the tissue, acquiring SOCT data from the tissue, and converting the SOCT data into at least one image.

In yet another aspect, the invention provides a method of forming an image of tissue that includes selecting at least one contrast agent, delivering the at least one contrast agent to tissue, acquiring SOCT data from the tissue, and converting the SOCT data into at least one image. The at least one contrast agent includes at least one water-soluble, biocompatible absorbing agent.

In yet another aspect, the invention provides a method of forming an image of tissue that includes determining the optical window of living tissue, selecting a laser spectrum range that is within the optical window, selecting at least one water-soluble, biocompatible absorbing agent that absorbs within the laser spectrum range, selecting at least one scattering agent that scatters within the laser spectrum range, delivering the at least one absorbing agent and the at least one scattering agent to the living tissue, acquiring SOCT data from the living tissue, performing time-frequency analysis on the data, performing spectral/pattern analysis on the data, retrieving the spatial distributions of the at least one absorbing agent and of the at least one scattering agent in the living tissue, and correlating the spatial distributions with at least one display parameter.

In yet another aspect, the invention provides a method of converting SOCT data into at least one image that includes performing time-frequency analysis on SOCT data from tissue, performing spectral/pattern analysis on the SOCT data, retrieving the spatial distribution of at least one contrast agent in the tissue, and correlating the spatial distribution with at least one display parameter.

The scope of the present invention is defined solely by the appended claims and is not affected by the statements within this summary.

BRIEF DESCRIPTION OF THE DRAWINGS

The invention can be better understood with reference to the following drawings and description. The components in the figures are not necessarily to scale, emphasis instead being placed upon illustrating the principles of the invention.

DETAILED DESCRIPTION

The present invention makes use of the discovery that contrast agents can be selected and delivered to tissue to provide for enhancement of the contrast in SOCT imaging. By the site-specific and molecule-specific introduction of absorbing agents and/or scattering agents, the invention improves OCT imaging quality, widens OCT usage areas, and provides a means of molecular imaging. The present invention also includes the use of both absorbing agents and scattering agents in the same tissue to enhance SOCT image contrast. In addition, it has been discovered that the contributions of an absorbing agent and a scattering agent to the optical properties of contrast-enhanced tissue can be quantified separately. SOCT imaging that incorporates and analyzes contrast agents according to the present invention can provide for improvements in the image quality and in the variety of tissues that can be analyzed.

The term "contrast agent" means any substance that changes the optical properties of tissue containing the substance. Optical properties that may be changed include absorbance, reflectance, fluorescence, birefringence and optical scattering.

The term "optical modification" means a change in one or more optical properties of radiation.

The phrase "contrast enhancement" means that an image produced with the enhancement shows a greater difference in optical properties between parts of the image, than an otherwise identical image produced without the enhancement.

The term "image" means data produced by receipt of electromagnetic radiation, which may or may not be formed into a picture viewable by the human eye. This includes images produced directly onto a medium such as film or video.

Figure 1:
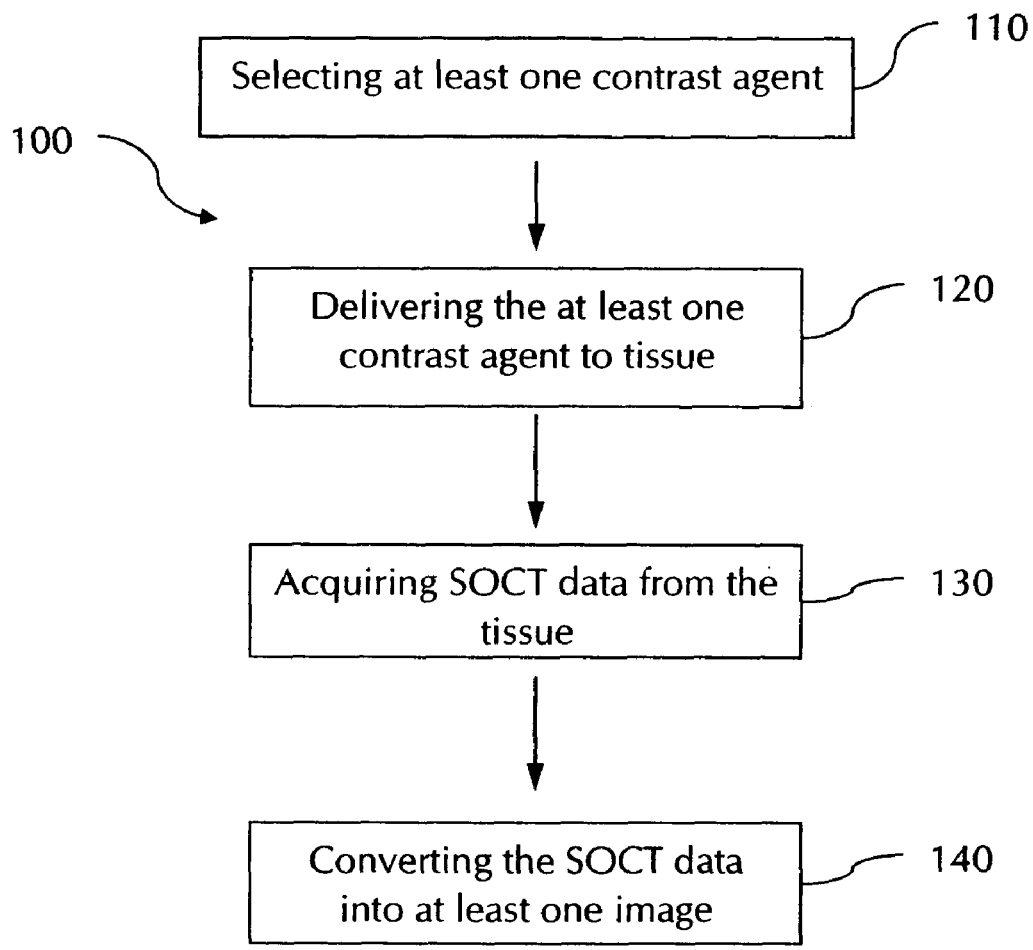
FIG. 1 depicts a method of forming an image of tissue.

FIG. 1 represents a method 100 of forming an image of tissue that includes selecting at least one contrast agent 110, delivering the at least one contrast agent to tissue 120, acquiring SOCT data from the tissue 130, and converting the SOCT data into at least one image 140. The selecting at least one contrast agent 110 may include selecting at least one absorbing agent and/or may include selecting at least one scattering agent.

Figure 2:
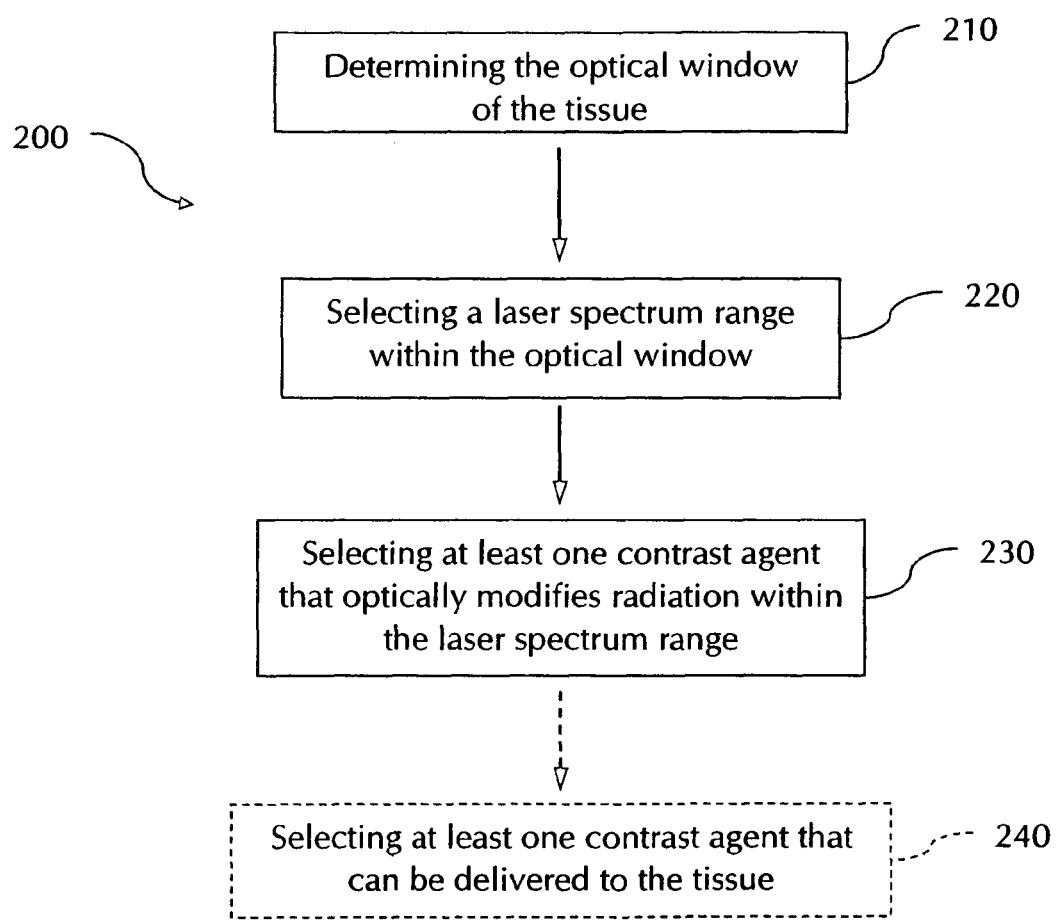
FIG. 2 depicts a method of selecting at least one contrast agent.

FIG. 2 represents a method 200 of selecting at least one contrast agent that includes determining the optical window of the tissue 210, selecting a laser spectrum range that is within the optical window 220, and selecting at least one contrast agent that optically modifies radiation within the laser spectrum range 230. If more than one contrast agent can be selected, the method 200 optionally may include selecting at least one contrast agent that can be delivered to the tissue 240.

Determining the tissue optical window 210 may include determining a wavelength region of electromagnetic radiation that is only minimally absorbed by the tissue. When radiation having a wavelength within this optical window is passed through the tissue, attenuation of the radiation is governed by scattering rather than absorbance. Ultraviolet radiation and infrared radiation are absorbed by the majority of substances in biological systems, such as water, proteins without chromophores, carbohydrates, nucleic acids and lipids. Accordingly, the tissue optical window for most tissues is in the near-infrared (NIR) region, typically from 600 nm to 1500 nm. Analysis within the tissue optical window is preferred for deep tissue imaging.

Selecting a laser spectrum range that falls within the tissue optical window 220 may include selecting a laser source that emits radiation over a wavelength range within the optical window. Preferably the center wavelength of the radiation is within the optical window. The radiation emitted by a laser may also be filtered or frequency shifted so as to produce radiation within the tissue optical window.

Selecting at least one contrast agent 230 may include selecting at least one substance that changes one or more optical properties of tissue containing the substance when subjected to radiation within the laser spectrum range. There must be overlap between the laser spectrum range and the spectrum range in which the substance optically modifies radiation. Selecting at least one contrast agent 230 may also include selecting at least two substances, each of which optically modifies radiation passing through the tissue. Preferably each substance modifies a different property of the radiation and/or modifies radiation within a different portion of the laser spectrum range.

Selecting at least one contrast agent that can be delivered to the tissue 240 may include determining the relative biocompatibility of each of the contrast agents that optically modify radiation within the laser spectrum range. Selecting at least one contrast agent that can be delivered to the tissue 240 may also include determining which of the contrast agents that optically modify radiation within the laser spectrum range can be combined with a delivery vehicle. This selection may include considerations such as stability of the contrast agent, since the agent should exhibit useful optical modification characteristics when present in the tissue for a period of time sufficient to perform the analysis. This selection also may include considerations such as tissue specificity. Certain contrast agents may be preferentially attracted to or absorbed by different types of tissue, making these agents useful for identifying these specific tissues. Certain contrast agents may be modified to make the agents specific to certain types of tissue or to increase specificity. For example, a non-specific contrast agent may be modified with an antibody that binds to a certain type of tissue, allowing for targeting of that tissue with the contrast agent.

The contrast agent may include at least one absorbing agent. Radiation that is backscattered from tissue containing an absorbing agent will have a spectrum different from that of the impinging radiation, since a portion of the spectrum has been absorbed by the absorbing agent in the tissue. Preferably an absorbing agent has an absorption profile that is sharp, meaning that the transition region from a wavelength region that is highly absorbed to a wavelength region that is subject to little or no absorption is narrow. A sharper absorption profile typically provides for increased analytical sensitivity. Sharp absorption profiles may also be useful if multiple absorbing agents are present, as this may provide for simultaneous analysis at different wavelengths.

Examples of absorbing agents include synthetic dyes and bio-engineered dyes. Both synthetic and bio-engineered dyes can have absorbance profiles in the near-infrared. Synthetic dyes typically are specific for small molecules and can be sensitive to pH or to concentrations of substances such as glucose, $CO_2$ and $O_2$. These dyes can be useful for detection of tumors, since hypoxia and acidity are two well-known characteristics of tumors that grow above a certain size. Specific examples of synthetic dyes include Indocyanine Green, fluorescein, SNARF and Fura Red. Indocyanine Green (Sigma-Aldrich) typically is used for retina angiography, fluorescein (Molecular Probes) typically is used for liver function testing, SNARF (Molecular Probes) typically is used as a pH indicator, and Fura Red (Molecular Probes) typically is used as a $Ca^{2+}$ indicator.

Bio-engineered dyes typically are specific for proteins or for specific cellular structures. Biological basic dyes are known to preferentially stain nuclei, allowing for determination of the nuclear-to-cytoplasm ratio, which is also an important indicator of tumor progression. Other examples of bio-engineered dyes include DNA binding dyes, dye-tagged immunoproteins and natural protein chromophores. Specific examples of bio-engineered dyes include Rhodamine tagged oligonucleotide and NN382 conjugated anti-human IgG. Rhodamine tagged oligonucleotide (EMP Biotech GmbH) typically is used for DNA sequencing and blotting, and NN382 conjugated anti-human IgG (LI-COR Inc.) typically is used for protein labeling.

Examples of absorbing agents also include particles such as quantum dots, nanospheres, nanorods and nanoshells. Specific examples of absorbing particles include metal-based nanoparticles, including nanoparticles containing gold, silver, copper, cobalt, nickel, iron, and alloys or mixtures thereof. Specific examples of absorbing particles also include plasmon-resonant nanoparticles, such as those described in copending U.S. patent application Ser. No. 10/753,972 to Boppart et al., filed Jan. 8, 2004, and published as US 2005/0171433 A1. Plasmon-resonant nanoparticles include metallic nanopaticles that have an extinction coefficient of at least $10^6$ $M^{-1}$ $cm^{-1}$ at some frequency in the infrared to ultraviolet spectrum (electromagnetic radiation in the frequency range of $10^{12}$ to $10^{17}$ Hz).

Examples of absorbing agents also include genetically expressed substances. For example, DsRed and hemoglobin are naturally occurring chromophores that have active near-infrared absorption and can be used as in vivo, non-invasive contrast agents. It is possible to introduce or induce overexpression of such chromophores in vivo by genetically modifying the experimental animal genome. For example, the local expression of DsRed can be achieved either by transfecting a strong promoter sequence followed by a DsRed producing gene, or by enhancing the natural DsRed producing mechanism. Examples of other genetically expressed absorbing agents include green fluorescent protein (GFP) and yellow fluorescent protein (YFP).

Absorbing agents may be encapsulated prior to delivery to the tissue. One useful aspect of encapsulation of absorbing agents is that non-biocompatible and/or water insoluble absorbing agents can be used. For example, microspheres containing absorbing agents may be constructed by encapsulating the absorbing agent in one or more layers of bovine serum protein. See, for example, copending U.S. patent application Ser. No. 10/463,833 to Suslick et al., filed Jun. 17, 2003, and published as US 2004/0258759 A1; and copending U.S. patent application Ser. No. 10/463,835 to Boppart et al., filed Jun. 17, 2003, and published as US 2004/0258762 A1. These microspheres may incorporate in their shells and/or in their cores a wide range of substances that can alter the local optical properties of tissue. The protein shell may also be functionalized to target agents to specific regions of interest.

The contrast agent may include at least one scattering agent in addition to the at least one absorbing agent. Examples of scattering agents include protein microspheres, microbeads and nanoparticles.

Protein microspheres have an exterior protein shell and an interior containing a gas, a liquid or particles. The compositions of the shell and the interior may be varied to produce microspheres having different spectral scattering properties. The spectral scattering properties may also be affected by the relative dimensions of the shell and the interior. See, for example, U.S. Patent Application Publication Nos. US 2004/0258759 A1 and US 2004/0258762 A1. The protein in the exterior shell can also be engineered such that melanin, gold or carbon particles are embedded. See, for example, Lee, T. M. et al., *Optics Letters,* 2003, 28(17), 1546-1548.

Simple microbeads having sizes close to the selected laser wavelength can provide Mie scattering of the laser radiation. This spectral scattering can be modified by coating the beads with dye or other materials.

Metal nanoparticle scattering agents may be solid particles or may be nanoshells. One advantage of metal nanoparticles over other scattering agents is the resistance of the nanoparticles to optical, chemical and/or thermal degradation, including denaturation and bleaching. In addition, biomolecules can be bound to nanoparticles using similar techniques to those used for gold colloids. Solid metal nanoparticles may be formed in a variety of shapes, which can affect the optical scattering properties. Metal nanoshells may have a core containing a dielectric material, and modifications in the shape, composition and relative dimensions of core and the shell can provide for systematic variation of the optical resonance over a broad wavelength region, ranging from near-UV to the mid-infrared. Gold nanoshells may be engineered to scatter or absorb light primarily in the wavelength ranges typically used for OCT.

Crystalline nanoparticles containing dielectric material may also be scattering agents. Examples of crystalline nanoparticles include Bragg reflectors and photonic crystals. Light traveling through these nanoparticles undergoes a periodic variation of the refractive index, causing a splitting of the bands at the edge of the Brillouin zone. These stop gaps appear as minima in the transmission and give rise to Bragg scattering, which is highly wavelength dependent.

Delivering the contrast agent to the tissue may be accomplished by a variety of methods. If the target tissue region is a relatively large area and can be easily accessed with a hypodermic needle, the contrast agent can be directly injected into the tissue. The contrast agent may then diffuse through tissues to create a region of high contrast. In some applications, the contrast agent can be delivered and targeted by intravenous injection. This may be useful when examining the circulatory system in tissue, when delivering the contrast agent systemically, or when the contrast agent is known to aggregate naturally in some organs or tissues. Examples of these analyses include retina angiography and analysis of liver tissue. If cells in the target tissue express specific antigens, delivery of the contrast agent may include using a contrast agent conjugated with antibodies for the antigen. For example, Cy-annexin can be conjugated with a contrast agent for tumor apoptosis studies. Examples of these modified contrast agents include commercially available targeting antibodies labeled with dyes specific for the near infrared range.

Acquiring SOCT data includes dividing low-coherence radiation between two paths, the reference path and the sample path. Radiation traveling along the reference path is reflected against a reference mirror and then collected as a reference signal. Radiation traveling along the sample path is reflected against a sample mirror and then into the sample tissue. Any radiation that is scattered back from the tissue sample is reflected against the sample mirror and then collected as a sample signal. The signals are filtered to match the dispersion and polarization and then combined into an interference pattern. The resulting interference pattern corresponds to the signal from a single point within the sample. The depth of this point is determined by the distance between the sample and the light source relative to the distance between the reference mirror and the light source, as constructive interference is maximized for signals having the same path length. Variation of these relative distances provides for signals from points at different depths within the sample. Two-dimensional in-plane translation of the sample signal relative to the sample can provide signals across a particular area of the sample.

A variety of techniques can be used to divide the laser radiation into two signals. For example, the radiation can be intersected by a partially reflective mirror, reflecting a portion of the radiation at an angle and permitting the remainder of the radiation to pass through the mirror. The radiation may also be passed through a fiber optic assembly that is configured to split the incident radiation into two fiber optic paths. Variation of the scan depth can be accomplished by moving the reference mirror and/or the sample along the path of the radiation. Variation of the lateral position of the scan can be accomplished by changing the angle of the sample mirror and/or by moving the sample.

Figure 3:
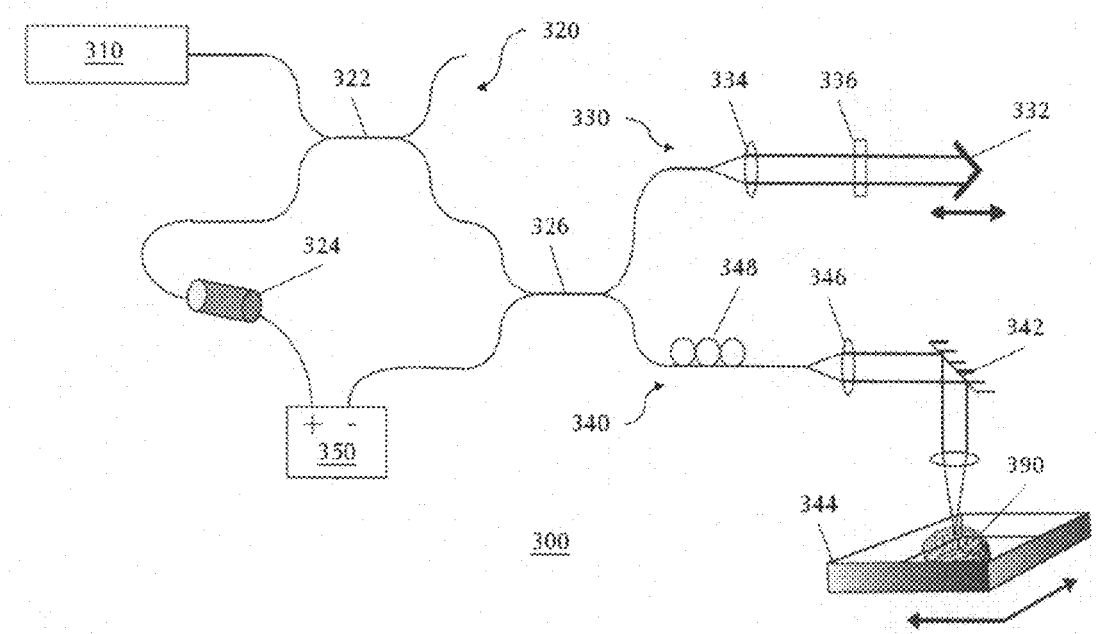
FIG. 3 is a schematic representation of a device for acquiring SOCT data.

FIG. 3 is a schematic representation of an example of a device 300 for acquiring SOCT data from a sample 390. SOCT device 300 includes a low coherence laser source 310, a fiber optic assembly 320, a reference assembly 330, a sample assembly 340 and a detector 350. The fiber optic assembly 320 may include a preliminary beam splitter 322 that diverts 10% of the radiation to adjustable attenuator 324 connected to the detector 350. The fiber optic assembly 320 includes a beam splitter 326 that divides the radiation between the reference assembly 330 and the sample assembly 340. The radiation that is reflected from the reference assembly 330 and the sample assembly 340 is directed to the detector 350. Reference assembly 330 includes reference mirror 332, which may be moved toward or away from the fiber optic assembly 320. The reference assembly 330 may include fiber collimator 334, for collection of the radiation reflected from the reference mirror 332, and may include a dispersion matching glass 336 to match the dispersion of the reference signal with the sample signal. The sample assembly 340 includes sample mirror 342, which reflects the radiation to the sample 390 in the sample holder 344. The orientation of the sample mirror 342 may be varied to provide for scanning of the radiation across an area of the sample. In addition to or instead of changes in the orientation of the sample mirror 342, the sample holder 344 may be moved along the length and width of the sample. The sample assembly 340 may include fiber collimator 346, for collection of the radiation reflected from the sample mirror 342, and may include a polarization matching paddle 348 to match the polarization of the sample signal with the reference signal. The detector 350 can perform initial processing of the signal to provide the SOCT data. Initial processing may include digitization, noise removal and digital aberration correction.

In one example of an SOCT device, the low coherence laser is a Nd:YVO$_4$ pumped titanium:sapphire source laser that has a spectrum span from 650 nm to 900 nm after passing through a non-linear fiber. Dispersion and polarization are matched in the reference and sample assemblies. A precision galvonometer is used to scan the reference mirror, and non-linearities in galvo speed are relatively small so that interferometric triggering methods are not required. Special fibers, a 3-dB splitter, lenses, signal filtering, and demodulation are used to support the broad optical and electronic bandwidths. The detector collects the full fringe data and digitizes the signal with an oversampling ratio of at least 2.

If the laser source has an ultra-broad spectrum, the imaging should be done in free space since fiber-optic components typically cannot accommodate the extremely broad spectra. A spectral domain OCT setup may also be used to improve the resolution. For applications involving real time analysis, a real time SOCT based on a field-programmable gate array (FPGA) implementation can be used. The SOCT sample radiation can be delivered to internal body locations with the use of fiber-optic probes and catheters.

Figure 4:
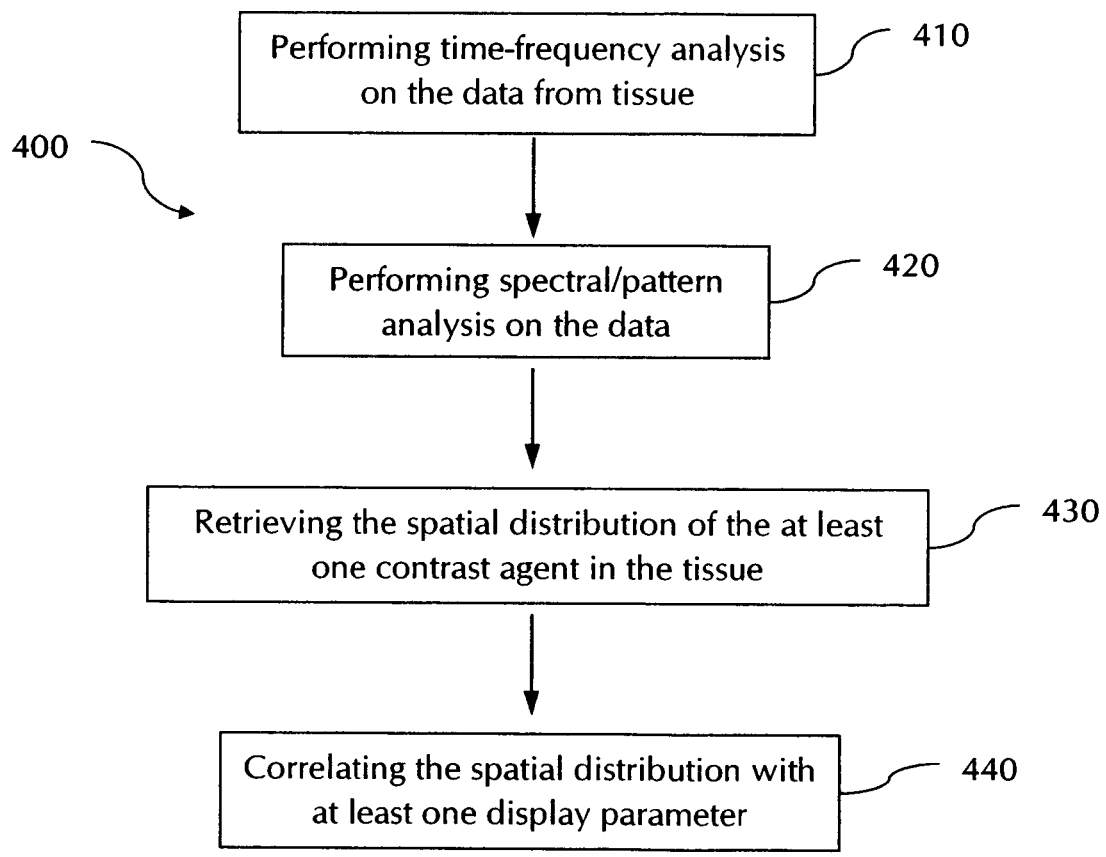
FIG. 4 depicts a method of converting SOCT data into at least one image.

FIG. 4 represents a method 400 of converting SOCT data into at least one image that includes performing time-frequency analysis on the data from tissue 410, performing spectral/pattern analysis on the data 420, retrieving the spatial distribution of the at least one contrast agent in the tissue 430, and correlating the spatial distribution with at least one display parameter 440.

Performing time-frequency (TF) analysis on the SOCT interference data 410 can provide advantages over conventional spectral analysis methods, such as the Fourier transform. Conventional methods typically are limited to use with stationary signals, whereas TF analysis offers localized spectral analysis useful for the non-stationary signals generated by SOCT. Time-frequency analysis in SOCT is described, for example, in Xu, C. et al. *Applied Optics*, 44, 1813-1822 (2005).

One aspect of TF analysis is the so-called time-frequency "uncertainty principle", which recognizes the tradeoff between spectral resolution and time resolution. Optimization of this time-frequency resolution may be facilitated by selection of appropriate TF analysis methods, referred to as time-frequency distributions (TFDs). For the case of only one strong scatter within the coherence length, the interferometric power spectrum $I(\omega, z)$ can be expressed as the multiplication of source spectrum $S(\omega)$ and the modulation effect, which includes the contributions from spectral backscattering profile $H_s(\omega)$, the lumped spectral absorption $H_a(\omega)$ by media before that scatter, and the total spectral modification $H_M(\omega)$ by optical components such as beamsplitter along the optical pathways. The equation for the interferometric power spectrum $I(\omega, z)$ is:

$$I(\omega,z)=S(\omega)H_s(\omega,z)H_a(\omega,z)H_M(\omega)$$

Usually $S(\omega)$ and $H_m(\omega)$ are stationary and known a priori, therefore measuring $I(\omega,z)$ offers the opportunity to study the material properties in the sample.

TFDs for SOCT can be classified into the categories of linear TFDs, Cohen's class TFDs and model-based TFDs. Linear TFDs are classical time-frequency analysis methods that only involve linear operations to the time domain signal. The short-time Fourier transform (STFT) and Gabor representations are the most familiar examples. The linear TFDs have the advantage that they are devoid of oscillating cross-terms, which are present for many other TFDs. Different TF tradeoffs can be made by choosing different time windows.

Linear TFDs often lead to good results, but they are compromised by the tradeoff between time and frequency resolution due to a windowing effect.

Cohen's class TFDs, also referred to as "bilinear TFDs," can be performed in many variations. One example of a Cohen's class TFD is the Wigner-Ville distribution (WVD), which can achieve better TF resolution than the linear TFDs. The main drawback with the WVD is the presence of strong cross-terms if the signal is multi-component. Cross-terms can be suppressed by using 2-D low-pass filters (kernels) in the ambiguity domain such as in the smoothed pseudo WVD (SPWVD). Another example of a Cohen's class TFD is a data-adaptive TFD that employs a radially-Gaussian kernel that is signal dependent, and thus changes shape for each signal (D. L. Jones and T. W. Parks, *IEEE Transaction on Acoustics, Speech and Signal Processing*, 38, 2127-2135 (1990)).

In model-based TFDs, the spectrum is not directly calculated. Instead, models and model parameters are estimated and used to reconstruct the spectrum. Models should be carefully chosen based on prior information. For example, if it is known that the dominating spectral modification occurring in a sample is due to the addition of a specific absorbing agent, a model can be constructed based on the laser spectrum and the absorbing agent absorption spectrum to extract the absorbing agent concentration distribution in the sample. If no prior knowledge is known, an autoregressive-moving average (ARMA) model is often used. The time localization of model-based TFDs is achieved by windowing.

The equation for the interferometric power spectrum $I(\omega, z)$ includes terms for the contributions from the lumped spectral absorption $H_a(\omega)$ by media before scattering and from the spectral backscattering profile $H_s(\omega)$. These two contributions have different requirements on the time-resolution and frequency-resolution. The spectral back-scattering is a short-range effect, in that large spectral variations can happen within a very short distance, usually between interfaces such as cell or tissue boundaries. High spatial resolution is required while spectral resolution can be somewhat relaxed because large spectral modifications are expected. In contrast, the spectral absorption or scattering loss is a relatively long-range effect following the Beer's absorption law. At typical absorber concentrations in tissue, distances larger than the coherence length of the optical source are typically required to produce significant spectral modification. Both effects may co-exist with tissue imaging.

Preferably, the TFD used to perform the TF analysis is optimized for resolving minute time-frequency variations. This optimization may include consideration of the various tradeoffs between different TFDs, the different parameter choices within TFDs, and the specific SOCT imaging application that is being considered.

For example, a comparison can be made between linear TFDs and Cohen's class TFDS. The linear TFD method STFT has a simple intuitive interpretation and by choosing windows of different lengths, different resolution tradeoffs can be made. Typically, however, one must manipulate the window depending on whether spectral variation or time variation are being estimated. For two interfaces that are very closely spaced, the STFT may be unable to resolve the components effectively. In contrast, Cohen's class TFDs typically can generate more compact TF analysis and therefore are more appropriate for imaging spectral reflections where higher time-frequency resolution is desired. However, the Cohen's-class TFDs suffer from the fact that artifacts are generated for multi-component signals. This problem may be mitigated by the fact that many kernel-based TFDs have significantly-reduced artifact level, and that the SOCT signals are usually narrow pass-band signals corresponding only to the laser spectrum used in the experiments. Frequently, the artifacts from TFDs are out of the pass-band and can therefore easily be removed by filtering.

Continuing this comparison of STFT and Cohen's class TFDs, the increase in joint time-frequency resolution offered by Cohen's-class TFDs is not necessarily optimal in all SOCT imaging applications. When imaging tissue absorption or when using low-concentrations of absorbing agents as contrast-enhancing agents, significant absorption frequently requires a long pathlength. For this case, even the STFT, with its lower spatial resolution, can be sufficient. Because the STFT is totally devoid of artifacts, this TFD is the most reliable for such applications. In addition, computing STFT is significantly faster than other TFDs because of the use of the fast Fourier transform (FFT). The flexibility of digital processing permits essentially arbitrary transformation. One could potentially run a fast and less accurate STFT first, identify the potential absorbing and spectrally-reflecting locations, and then run different TFDs in the desired regions to obtain the best information. When the scattering agents are very close together and comparable to the coherence length, usual spectral analysis methods may not be reliable, as it may not be accurate to assume that the frequency components shown on the TFD plots are actually the frequency components representative of that particular spatial point. Instead, pattern analysis algorithms are better suited for identifying different objects. Digital signal processing algorithms applied to experimentally-acquired SOCT data may provide advantages in extracting diagnostic and quantitative information.

Performing spectral/pattern analysis on the SOCT interference data 420 can separate the signal due to the absorbing agents from the signal due to the scattering agents. Spectral analysis is based on the difference between the individual spectral features of the contrast agents and the individual spectral features of the endogenous material. Pattern analysis is based on the overall spectral profiles of the contrast agents. For example, the absorbing and/or scattering spectrum of a contrast agent may have a unique combination (i.e. "pattern") of modulations and features that can be matched against known optical profiles. Both spectral analysis and pattern analysis can provide for extraction of useful data regarding the presence and location of the contrast agents within tissue.

Figure 5:
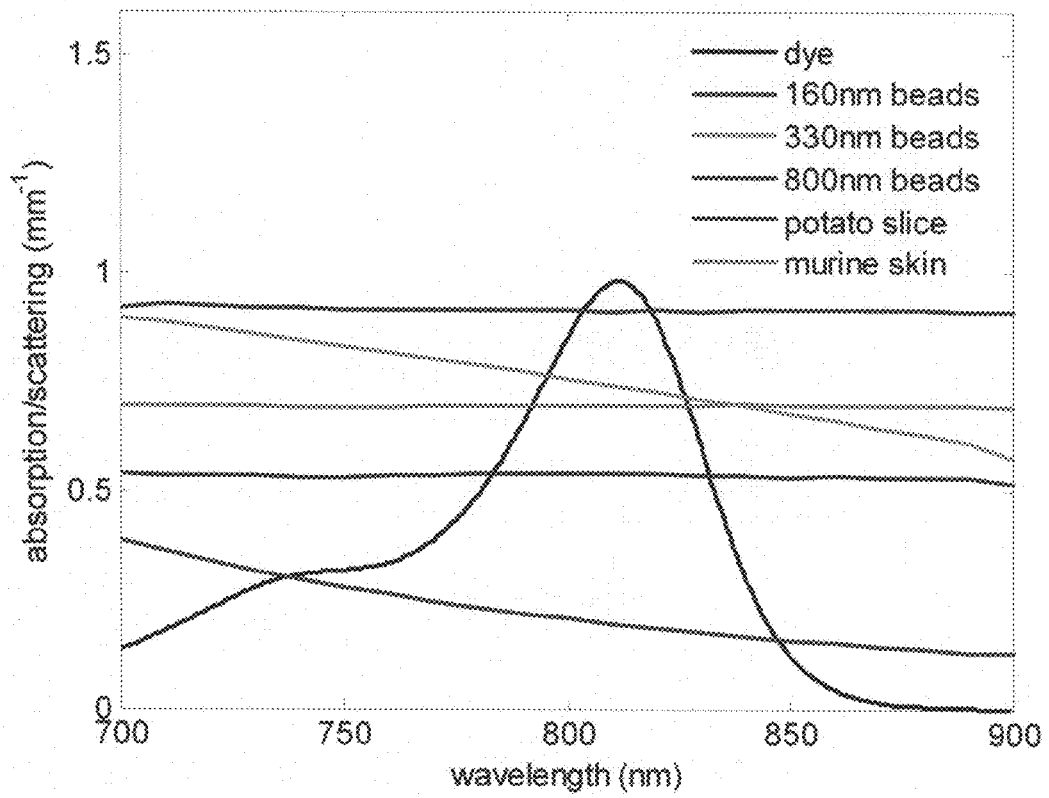
FIG. 5 is a graph of scattering loss for a series of microbead solutions and tissue samples, together with a graph of absorption attenuation for an absorbing agent solution.

In one example of spectral/pattern analysis, the SOCT data examined is from a relatively homogenous tissue sample containing an absorbing agent having a known spectrum. This type of spectral/pattern analysis is described, for example, in Xu, C. et al. *Opt. Express* 12, 4790 (2004). The homogeneity provides for scattering spectra of endogenous scattering agents that are similar among different tissue layers. The scattering profile of endogenous scatterers in this case is mostly a linear function. For example, FIG. 5 is a graph of scattering loss as measured by a spectrometer for a series of microbead solutions (1% solution of 160 nm silica microbeads; 0.5% solution of 330 nm silica microbeads; and 0.5% solution of 800 nm silica microbeads) and for tissue samples of a thin potato slice and of murine skin. This graph also includes the absorption attenuation of a 40 μM solution of the near-infrared dye ADS830WS (American Dye Sources, Inc.). All specimens examined showed that scattering loss was linearly dependent on wavelength, with correlation coefficients ranging from 0.987 to 0.999. In comparison, the correlation coefficient for the absorbing agent absorption profile was measured at 0.202. This spectral difference can be used to separate the contribution of the absorbing agent from the contribution of the scattering agent.

One possible method for separation of the absorbing agent from the scattering agent in this spectral/pattern analysis is the "least-squares fitting" algorithm. If the wavelength dependent factors are eliminated from the interferometric power spectrum $I(\omega, z)$ equation, the interference signal may be expressed as:

$$I'(\lambda, z) \triangleq I(\lambda, z)/I(\lambda, z = 0)$$
$$= R'(z)\exp\left\{-2\int_0^z [\mu_a(\lambda, z') + \mu_s(\lambda, z')]dz'\right\}$$

Because the same NIR dye of high absorptivity is used, the absorption coefficient at certain depths depends only on the absorbing agent concentration present at that depth. Assuming the scattering agents have similar spectral loss along sample depth, for the first-order approximation, both $\mu_a(\lambda, z)$ and $\mu_s(\lambda, z)$ are separable functions in $\lambda$ and z:

$$\mu_a(\lambda,z) = \in_a(\lambda) f_a(z)$$

$$\mu_s(\lambda,z) = \in_s(\lambda) f_s(z)$$

where $f_a(z)$ represents the absorbing agent concentration and $f_s(z)$ represents the scattering agent concentration at a particular depth z. The functions $\in_a(\lambda)$ and $\in_s(\lambda)$ represent the absorption and scattering per unit concentration and per unit pathlength, and can be measured by a laboratory spectrometer or by integrating spheres. Substitution of these $\in(\lambda)$ expressions into the interference signal expression, followed by taking the logarithm of both sides yields:

$$Y(\lambda, z) \triangleq \log[I'(\lambda, z)]$$
$$= \log R'(z) - 2\left[\varepsilon_a(\lambda)\int_0^z f_a(z')dz' + \varepsilon_s(\lambda)\int_0^z f_s(z')dz'\right]$$
$$= -\varepsilon_a(\lambda)F_a(z) - \varepsilon_s(\lambda)F_s(z) + C(z).$$

Thus, $F_a(z)$, $F_s(z)$, and $C(z)$ are wavelength independent functions to be found. The values of $Y(\lambda, z)$ may be obtained by time-frequency analysis of the SOCT data.

The $Y(\lambda, z)$ equation typically can only be solved with some optimality criteria due to the presence of noise and other non-ideal conditions. In one example, weighted minimal-mean-square-error (MMSE) optimization provides an unbiased optimization and has minimum-variance properties. After application of an estimation error variable using a weighting function that emphasizes the more accurate data, the least squares solution is:

$$\underbrace{\begin{bmatrix} \int_{\lambda_1}^{\lambda_2} \varepsilon_a^2(\lambda)W(\lambda)d\lambda & \int_{\lambda_1}^{\lambda_2} \varepsilon_s(\lambda)\varepsilon_a(\lambda)W(\lambda)d\lambda & \int_{\lambda_1}^{\lambda_2} \varepsilon_a(\lambda)W(\lambda)d\lambda \\ \int_{\lambda_1}^{\lambda_2} \varepsilon_a(\lambda)\varepsilon_s(\lambda)d\lambda & \int_{\lambda_1}^{\lambda_2} \varepsilon_s^2(\lambda)W(\lambda)d\lambda & \int_{\lambda_1}^{\lambda_2} \varepsilon_s(\lambda)E(\lambda)d\lambda \\ \int_{\lambda_1}^{\lambda_2} \varepsilon_s(\lambda)W(\lambda)d(\lambda) & \int_{\lambda_1}^{\lambda_2} \varepsilon_s(\lambda)W(\lambda)d\lambda & \int_{\lambda_1}^{\lambda_2} W(\lambda)d\lambda \end{bmatrix}}_{A}$$

$$\underbrace{\begin{bmatrix} -F_a(z) \\ -F_s(z) \\ C(z) \end{bmatrix}}_{X} = \underbrace{\begin{bmatrix} \int_{\lambda_1}^{\lambda_2} Y(\lambda, z)\varepsilon_a(\lambda)W(\lambda)d\lambda \\ \int_{\lambda_1}^{\lambda_2} Y(\lambda, z)\varepsilon_s(\lambda)W(\lambda)d\lambda \\ \int_{\lambda_1}^{\lambda_2} Y(\lambda, z)W(\lambda)d\lambda \end{bmatrix}}_{Y}.$$

Matrix Y is obtained from the SOCT measurements. System matrix A is independent of depth z. Once $F_a(z)$, $F_s(z)$, and $C(z)$ of matrix X are solved, the absorbing agent concentration profile $f_a(z)$ and the scattering agent profile $f_s(z)$ can be solved using the definitions:

$$F_a(z) \triangleq 2\int_0^z f_a(z')dz',$$

$$F_s(z) \triangleq 2\int_0^z f_s(z')dz',$$

$$C(z) \triangleq \log R'(z).$$

There are typically two experimental scenarios in SOCT. The first scenario involves structures that have distinctive layers, such as experiments with cuvettes or layered phantoms. For this scenario, the parameters for time-frequency analysis may be chosen for less time resolution but higher spectral resolution. Far-spaced distinctive z points may be taken, and the least squares matrix can be solved. The second scenario involves structures that do not have distinctive layers, such as biological tissues or inhomogeneous phantoms without apparent layering. For this scenario, appropriate time-frequency analysis should be chosen with the parameters optimized to meet specific needs. Cumulative absorption $F_a(z)$ and scattering $F_s(z)$ may be calculated, providing for retrieval of the absorbing agent profile $f_a(z)$ and scattering agent profile $f_s(z)$.

In another example of spectral/pattern analysis, the SOCT data examined is from a tissue sample containing multiple scatterers, which may include endogenous scatterers and exogenous contrast agents. The SOCT analysis may be combined with analysis methods from light scattering spectroscopy (LSS). This type of spectral/pattern analysis is described, for example, in Xu, C. et al. *Opt. Express* 13, 5450 (2005), and in Xu et al. *Opt. Lett.* 31, 1079, (2006). The imaging volume represented by a voxel in a standard OCT image is defined by the Gaussian beam width and the coherence gating, centered at the nominal voxel position. The voxel intensity is a coherent sum of scattering from all scatterers inside the imaging volume. In SOCT, due to the time-frequency uncertainty principle, in order to achieve reasonable spectral resolution, the imaging volume is usually considerably larger than in standard OCT. The imaging volume in SOCT is defined by the Gaussian beam width and the coherence gating of a particular spectral sub-band (or the time window length if the STFT is used). Although the imaging volume in SOCT is larger than in standard OCT, the single scattering approximation still holds for most cases.

Assuming all single-scattering events, the collected OCT signal intensity from N scatterers inside an imaging volume in the spectral domain is $$|I(k_0)| = |C(k_0)| \left| H(k_0) * \sum_{n=1}^{N} S_n(k_0, P_n) \right|$$

where H is the Fourier transform of the time window, described as a spatially dependent function h<z>. The function $S(k_o, P)$ represents the field coupled back into the lens, and is the sample-arm field for the OCT interferometer. Calculating this by integrating the secondary sources over the collection beam profile, and simplifying due to the use of the same set of optics for illumination and collection, provides $$\sum_{n=1}^{N} S_n(k_0, P_n) =$$

$$\sum_{n=1}^{N} \int \int C(k_o) F_i(q_i) F_i^*(q_a) e^{i[r_a \cdot (k_i - k_a)]} R(k_i, k_a, k_o, P_n) d^2 k_i d^2 k_s$$

where $R(k_i, k_s, k_o, P_n)$ represents the wavelength-dependent scattering amplitude of the n-th scatterer located at the origin.

These equations indicate that the scattering-mode SOCT signal may be obtained from a coherent superposition of the fields scattered from many plane waves and by many scatterers. In standard LSS, particle size is determined by observing the spectrum of the scattered field and matching the spectral signature to a particular particle size. The spectral interference arising from the coherent superposition may make such a procedure complicated for scattering-mode SOCT, since the measured OCT spectral intensity typically has a modulation term that depends on the number and the positions of the scatterers. Algorithms may be used to jointly estimate the scatterer property and location. In one example, when it is known a priori that the sample consists of practically identical particles, many incoherent SOCT measurements may be averaged. Conventional LSS may perform this incoherent averaging by using a large beam width and spatially-incoherent light sources. In a second example, an over-sampling procedure may allow an accurate estimation of particle size when one expects only one large scatterer surrounded by many smaller scatterers within the SOCT voxel.

Scatterers may be sized based on the measured spectra. For example, one approach is based on pitch detection such as using the Fourier transform or determining the autocorrelation. The principle behind this approach is that the oscillation "frequency" in the wavelength-dependent scattering is size dependent, such that larger scatterers tend to produce more oscillatory patterns. A second approach is based on curve fitting such as using least-square or $c^2$ methods. This second approach provides an exhaustive search of possible scattering sizes and attempts to fit the normalized experimental measurement to the theoretical prediction.

In many cases, tissue demonstrates layered or regional structure where adjacent scatterers (either in axial or transverse directions) are more or less homogeneous. If weak focusing (low NA) is used, the actual single-scatterer spectral scattering may be resolved by extensive incoherent averaging. Although OCT is typically referred to as a coherent high-spatial resolution imaging method, there are several occasions when incoherent averaging is possible over adjacent scan lines. Incoherent averaging is also possible by utilizing many so-called "diversity" methods used in OCT speckle-reduction, such as polarization or angular diversity.

Perhaps the most common SOCT scenario in biological imaging is that of one large scatterer surrounded by several small scatterers. For example, cells may have only one nucleus, but may have several mitochondria and multiple other small scatterers. It is often desirable to resolve the wavelength-dependent scattering due to the large scatterer in the presence of these smaller scatterers. For many cases, the spectrum measured by SOCT in this scenario depends on the exact location of the large scatterer within the imaging beam. If the large scatterer is in the center of the beam, the scattering is dominated by the larger scatterer. When the large scatterer is gradually moved off-center from the central region of the Gaussian beam, the scattering profile for the large scatterer is gradually corrupted by the modulation effect due to the presence of the small scatterers. This means that in some cases, the scattering due to the large scatterer can be resolved by over-sampling the SOCT signal while transverse scanning, followed by a computational search for the signal maximum.

Retrieving the spatial distribution of the at least one contrast agent in the tissue 430 includes selecting a parameter that correlates with the value of the absorbing agent profile or the scattering agent profile at a given point, followed by quantifying that parameter. Examples of quantifiable parameters include the spectral centroid shift, the Beer's law determination of spatial distribution, and correlation strength with expected spectra. These spatial distributions may be retrieved for some or all of the scanned positions within the tissue.

The spectral centroid of SOCT interference data that has been analyzed by TFD is expressed as:

$$Centroid(z) = \frac{\int_0^\infty \omega g TFD(\omega, z) d\omega}{\int_0^\infty TFD(\omega, z) d\omega}$$

The spectral centroid location and its shifting property can be used as a parameter to characterize the contrast agent distribution. For example, if there is a particular absorbing agent in one location that absorbs preferentially low frequency light, then the spectral centroid determined by the TFD of the data from that location will be shifted toward higher frequency.

The Beer's law determination of concentration can be used, assuming that the system can be regarded as a purely absorbing region that follows Beer's law. The magnitude of $H(\omega)$ expressed in wavelength can be written as a function of the depth z in the sample:

$$H(\lambda, z) = \exp\left[-\int_{z_1}^{z_2} 2z \cdot \mu(\lambda, z) dz\right]$$

Assuming the spatial analysis window is from $z_i$ to $z_{i+1}$, then:

$$\int_{z_i}^{z_{i+1}} \alpha(\omega, z') dz' = \frac{1}{2} \ln \frac{|H_i(\omega, z)|}{|H_{i+1}(\omega, z)|}$$

Solving this integral equation by stepwise approximation, provides α(ω,z)dz, which is a quantifiable parameter.

Correlating the spatial distribution with at least one display parameter 440 includes assigning the values measured by the SOCT data to parameters that can be combined into a single display. For example, the two sets of values to be displayed may be the backscattering intensity, determined by the scattering agent profile $f_s(z)$, and the spatial distribution of the contrast agent. These values may then be plotted in two-dimensions, corresponding to a plane within the tissue.

Figure 6:
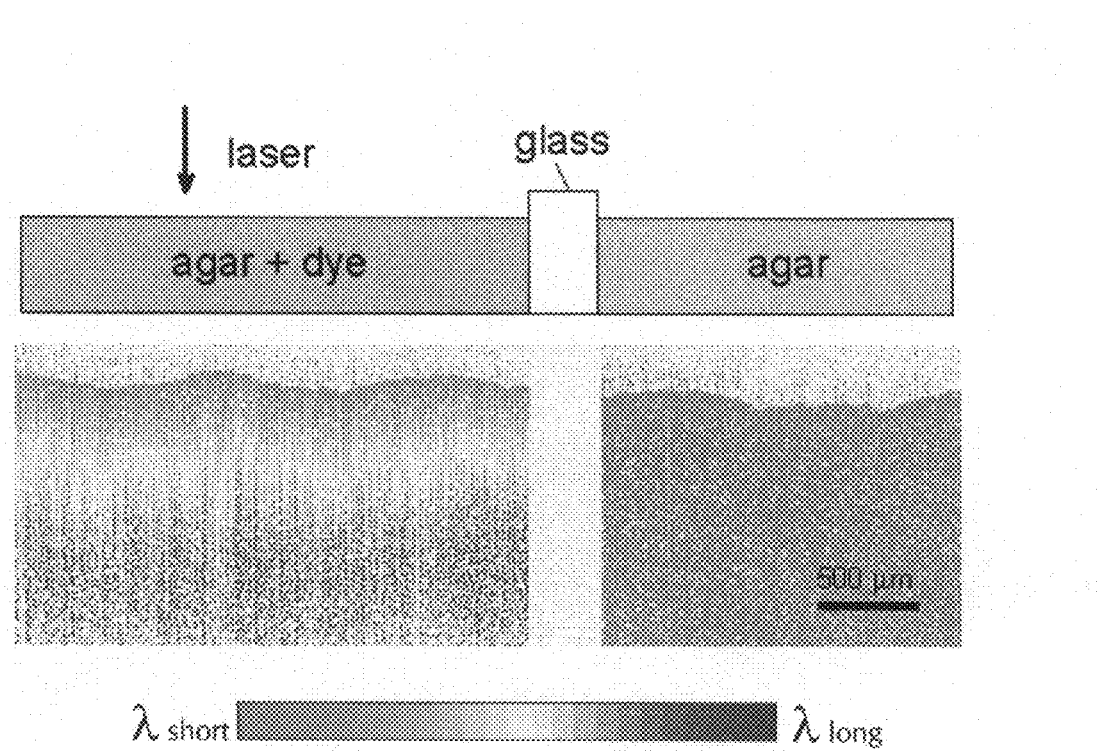
FIG. 6 is a schematic representation of a phantom sample and of a display of an SOCT image of the sample.

In one example, an agar phantom sample containing an absorbing agent on one side and no absorbing agent on the other side was imaged by SOCT. FIG. 6 is a schematic representation of the sample, together with a color display of the SOCT image. A hue-saturation-luminance color space was used to map the backscattering intensity I(x,z) into the saturation parameter and to map the absorbing agent spatial distribution into the hue, keeping the luminance constant. This approach permitted the intensity and the spectral parameters of the backscattered light to be visualized in a 2D map. When absorbing agent is present, and with increasing depth, the short wavelengths components of the backscattered spectrum are more strongly absorbed, giving a red-shift hue for greater depths. When the absorbing agent is not present, no significant change is found.

The following examples are provided to illustrate one or more preferred embodiments of the invention. Numerous variations can be made to the following examples that lie within the scope of the invention.

EXAMPLES

Example 1

SOCT Device

A fiber-based OCT setup was used for these studies. A diode-pumped mode-locked titanium:sapphire laser source with a center wavelength around 780 nm was used as the optical source. This laser pumped an ultrahigh numerical aperture (UHNA4, Nufern) fiber to spectrally broaden the output bandwidth to 120 nm. Dispersion and polarization were matched in the interferometer arms. A precision linear optical scanner was used to scan the reference arm, and the small nonlinearity (less than 0.5%) was corrected by calibration. The axial resolution of this system was measured to be 3 μm in air. A high-speed (5 Mega-samples per second, 12-bit) analog-digital converter (NI-PCI-6110, National Instruments) was used to acquire interferometric fringe data. Axial scans containing the interferometric signals were sampled at 100,000 data points, and at 512 transverse positions to form two-dimensional images.

The collected data were analyzed using Matlab for envelope detection and depth-resolved spectroscopic information. Time-frequency analysis was performed using the short-time Fourier transform (STFT). For experiments in which high depth resolution was not required, a STFT window size of 16,384 points (corresponding to a length of 327 μm in air) was chosen to allow for spectral resolution of 1 nm. For experiments in which both spectral resolution and depth resolution were required, the STFT window size was chosen to optimize the time-frequency concentration, typically using 1024 points (20 μm in air). To increase the signal-to-noise ratio when recovering the absorbing agent absorption spectrum, the absorption spectra calculated was averaged over 512 measurements in cases in which lateral resolution was not required.

Example 2

Absorbing Agent Selection

As noted in Example 1, a diode-pumped mode-locked titanium:sapphire laser source was selected as the optical source, due to its center wavelength around 780 nm. This wavelength, and the 120 nm window of the ultrahigh numerical aperture fiber, provided for imaging of tissue due to the transparency of most tissue components in this wavelength window.

Figure 7:
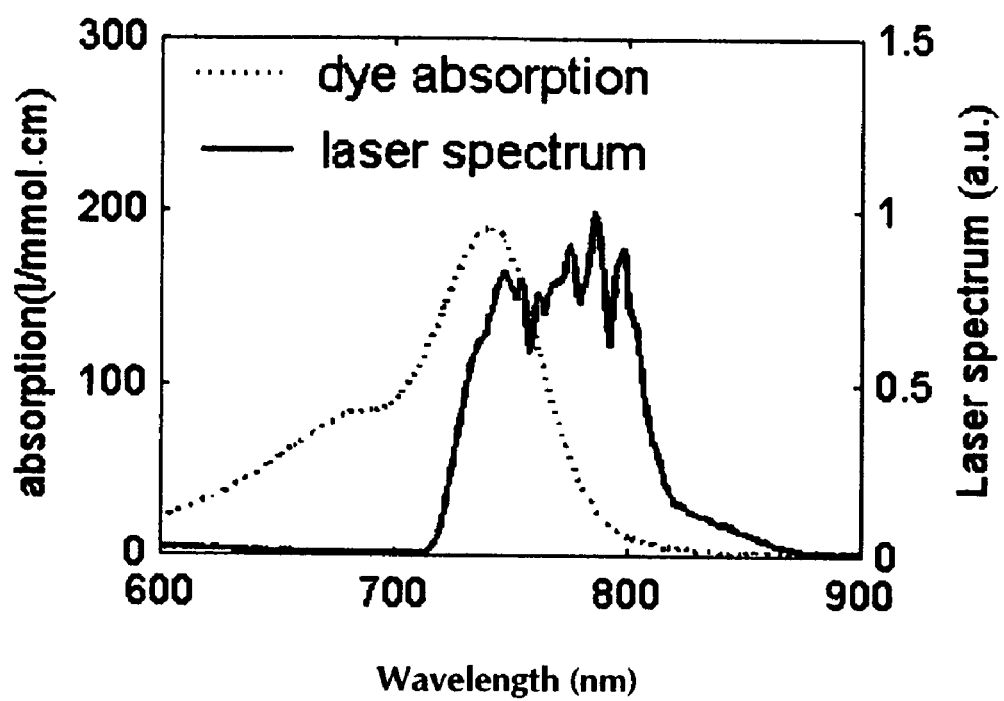
FIG. 7 is a graph of the emission spectrum of a laser, together with the absorption spectrum of an absorbing agent.

A near-IR (NIR) absorbing agent was selected based on the spectrum of the optical source. The NIR dye ADS7460 (H.W. Sands, Inc.) has a sharp peak at 740 nm. FIG. 7 is a graph of the emission spectrum of the laser (solid line) compared to the absorption spectrum of the absorbing agent (dashed line). As shown in FIG. 7, the absorbing agent, when used in appropriate concentrations, absorbed the shorter half of the laser spectrum wavelengths and transmitted the longer half, producing a predictable spectral signature. This absorbing agent could also be encapsulated within protein microspheres, which could be used as delivery vehicles. For example, the absorbing agent could be encapsulated within bovine serum albumin microspheres.

Example 3

Characterization of Absorbing Agent

Various concentrations of absorbing agent solution containing the dye of Example 2 were prepared. These solutions were placed in 1-mm thick glass cuvettes (QS-459, Nova Biotech) and imaged with SOCT. The interference data from light scattered back from the top and bottom absorbing agent-glass interfaces were recorded and analyzed to extract the spectra. The absorption spectrum of the absorbing agent solution was obtained using Beer's Law, as outlined by Faber et al (D. J. Faber, E. G. Mik, M. C. G. Aalders, and T. G. van Leeuwen, *Opt. Lett.* 28, 1436 (2003)). The centroid of the backreflected light spectrum was calculated in order to display the spectroscopic data in a color image.

Figure 8:
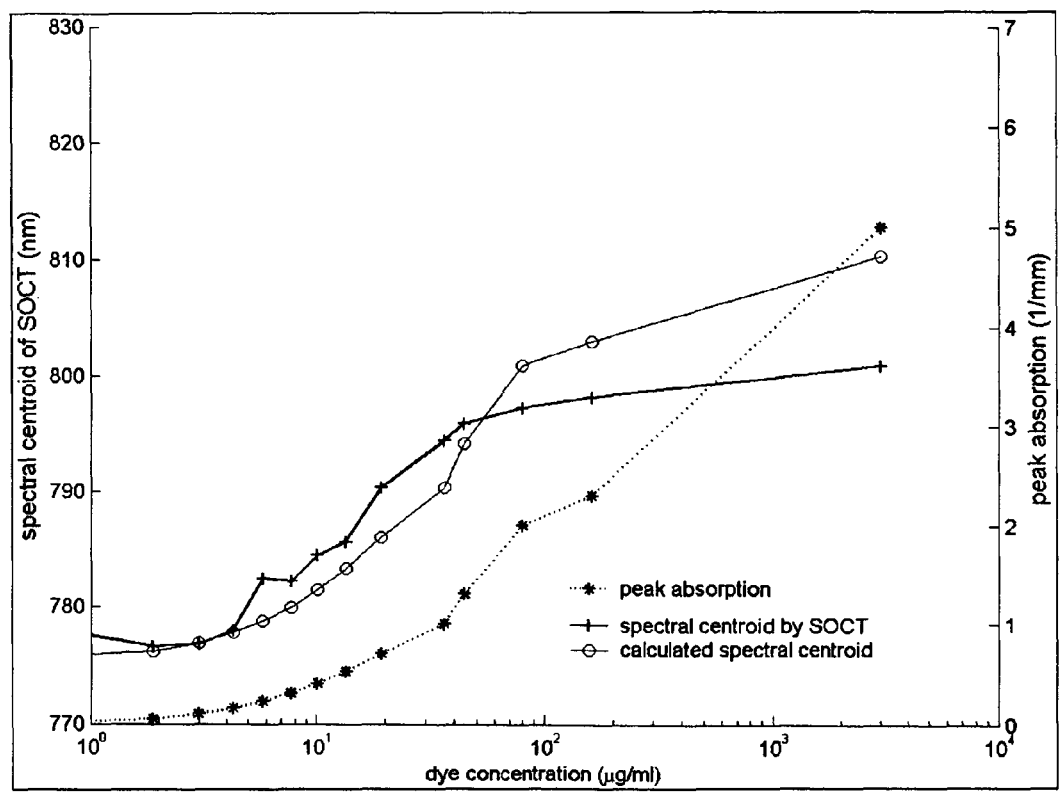
FIG. 8 is a graph of the centroid of a backreflected light spectrum as a function of absorbing agent concentration.

FIG. 8 is a graph of the centroid of the backreflected light spectrum as a function of the absorbing agent concentration. The dotted curve shows the peak absorption at 740 nm measured by a spectrometer. The shift of the spectral centroid increased and then reached a plateau with increasing absorbing agent concentration. The increase corresponded well to the theoretical calculation based on absorption data. Because OCT typically has penetration depths of 1-2 mm, an absorbing agent concentration of 50 μg/mL could produce the largest usable shift within this depth. At this concentration, most of the spectral center-of-mass shift occured within 1 mm. A further increase in the concentration would limit the penetration depth of SOCT applications, whereas a decrease in the concentration would reduce the amount of spectral centroid shift.

An agar sample was prepared with two distinct vertical columns separated by a glass wall to prevent diffusion between the columns. One column contained an absorbing agent concentration of 50 μg/mL, and the other column contained no absorbing agent. An equal concentration of 0.2% Intralipid solution was added to both columns for use as a scattering agent. The resulting false-color hue-saturation SOCT image showed that the spectrum of the backreflected light from the column containing the absorbing agent had shifted toward longer wavelengths with increasing depth, whereas this effect was negligible for the column without the absorbing agent.

Example 4

SOCT Imaging of Tissue

Figure 9:
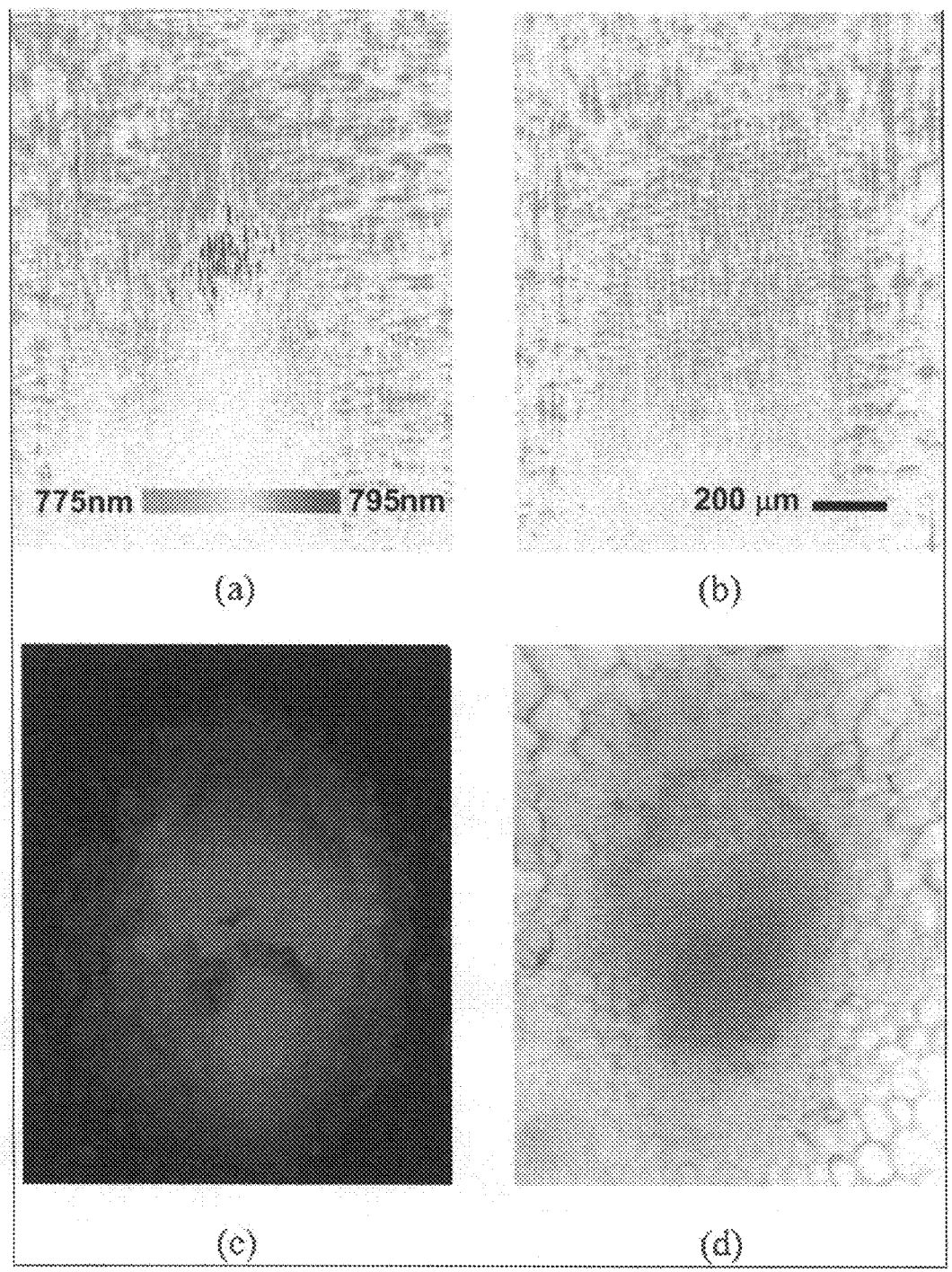
FIG. 9 is a series of images of the tissue of a celery stalk.

A stalk of green celery (*Apium graveolens* var. *dulce*) was imaged by SOCT. A celery stalk was cut near the root, leaving the upper leaves intact to facilitate transpiration. The celery stalk contained two distinct tissue structures. The bulk of the stalk was composed of collenchyma tissue, in which most of the cells were relatively large in size with thickened cell walls that mechanically supported the stalk. Distributed around the center of the stalk were vascular bundles in which the cells were relatively smaller in size and formed conducting vascular tubes to transport water and nutrients between the roots and leaves. These tissues were observed using light microscopy, as shown in FIG. 9D, in which the vascular bundle is in the center and is surrounded by collenchyma tissue.

An absorbing agent mixture was prepared by combining 10 mL of a 50 µg/mL mixture of the NIR dye of Example 2 with 0.5 mL of a 200 µg/mL mixture of Rhodamine 5G. A control image of the celery stalk was taken with SOCT before application of the absorbing agent. This control image is shown in FIG. 9B. The root end of the stalk was then submerged in the absorbing agent mixture for 4 h to allow for capillary transportation. After the absorbing agent mixture had been transported, the stalk was imaged by SOCT at the same location as the control image. This contrast enhanced SOCT image is shown in FIG. 9A. The celery stalk was cut in cross section at the SOCT imaging location and imaged by fluorescence microscopy (FIG. 9C) and light microscopy (FIG. 9D). Fluorescence microscopy was permitted by the Rhodamine in the absorbing agent mixture. The single-photon absorption spectrum for Rhodamine was outside of the titanium:sapphire laser spectrum, and the two-photon absorption and emission efficiency was extremely low ($<10^{-10}$), resulting in no detectable contribution to the SOCT signal.

When imaged by SOCT without an absorbing agent, no significant difference in the spectral center of mass was observed between the two types of tissues. The contrast between the two tissues was enhanced by the presence of the NIR absorbing agent. This contrast enhancement was apparent in the vascular regions containing the NIR absorbing agent, where strong shifting of the spectral centroid occurred. In FIG. 9A, the color bar represents the correspondence between pseudocolor labeling and the spectral centroid shift in the image. The surrounding avascular collenchyma tissue showed minimal changes. The vascular bundle region showing strong SOCT contrast enhancement also correlated well with the region showing strong fluorescence (FIG. 9C).

Example 5

Comparison of TFD Performance on Simulated SOCT Signals

Synthetic signals were generated in order to produce a comprehensive class of SOCT-like signals controlled by several parameters. Their design was based on the equation for the interferometric power spectrum $I(\omega, z)$:

$$I(\omega,z)=S(\omega)H_s(\omega,z)H_a(\omega,z)H_m(\omega)$$

To simplify the simulation parameters, the sampling time and reference arm translation speed were adjusted such that the 800 nm laser wavelength corresponded to a digital frequency of 0.125 Hz. Axial depth was converted to a signal acquisition time from 0 sec to 1 sec. Although an experimental OCT system would acquire axial scans much faster, these numerically-simple parameters were used without losing theoretical generalities.

Three different imaging scenarios were considered. The first scenario was a Gaussian pulse with a spectrum centered at 800 nm and a FWHM of 100 nm. This synthetic signal corresponded to a typical SOCT signal from a perfectly-reflecting mirror, and was used for testing TFD performance on minimal time-frequency spread. The second scenario was two consecutive "spectrally absorbed" Gaussian pulses, in which the first pulse contained all of the frequencies of the optical source, and the second pulse contained only the lower half of the frequencies of the optical source. This scenario corresponded to two closely-spaced reflecting interfaces with different spectral reflection profiles. By varying the distance between the pulses, this scenario was used for testing the minimal spatial separation of TFDs given a prior requirement on frequency resolution. The third scenario was a consecutive Gaussian pulse sequence with random positioning and a slowly varying spectrum between pulses, representing a region of homogeneous absorption and scattering. The absorbing agents were assumed to uniformly absorb upper half frequencies, following Beer's law. This sequence corresponded to SOCT signals scattering back from tissue with a roughly uniform scattering agent distribution but with high absorbing agent concentrations, and was used for testing the ability of the TFDs to retrieve the absorption coefficient of the media.

The synthetic signals were subjected to TF analysis using different TFDs. The TFDs of the signal on the TF plane were generated as color-scale images. In the cases where the distribution has negative or complex values, the magnitude was taken. For each of the TFDs, parameters were optimized by extensive parameter searching to represent the best possible outcome using that type of TFD. In cases in which good criteria were difficult to obtain, such as when lowering the cross-terms compromised the resolution of the auto term, qualitative evaluation was used to produce the best analysis.

To compare the overall quality of the TFDs on the synthetic signal from the first scenario, two criteria were used. The first criterion was the time-frequency spread (by measuring standard deviation) of the TFDs. The second criterion computed the unitless TF "concentration" or "sharpness" using the equation:

$$C = \frac{\iint_{\infty} |TFD(t,f)|^4 \, dt\, df}{(\iint_{\infty} |TFD(t,f)|^2 \, dt\, df)^2}$$

which is the fourth power of the $L_4$ norm divided by the squared $L_2$ norm of the magnitude of the TFD. See D. L. Jones and T. W. Parks, *IEEE Transaction on Acoustics, Speech and Signal Processing*, 38, 2127-2135 (1990). The testing results of TFDs on this synthetic signal are listed in Table 1. The linear TFD examined was the STFT with a Hamming window ("STFT"); the Cohen's class TFDs examined were WVD and Morlet wavelet ("WT"); and a Gaussian model was used for the model-based TFD ("Model-based"). The WVD achieved the best time-frequency concentration. Because signal model was exactly known for synthetic signal, model based TFD completely recovered the ideal TFD.

TABLE 1

TF resolution of TFDs on synthetic signal from first imaging scenario

|  | Ideal TFD | STFT | WT | WVD | Model-based |
|---|---|---|---|---|---|
| Time spread (s) | 0.027 | 0.032 | 0.040 | 0.020 | 0.027 |
| Frequency spread (Hz) | 0.016 | 0.032 | 0.038 | 0.022 | 0.017 |
| Time-frequency product ($10^{-4}$) | 4.32 | 10.2 | 15.2 | 4.40 | 4.59 |
| Concentration | 250 | 102 | 132 | 305 | 250 |

To compare the overall quality of the TFDs on the synthetic signal from the second scenario, two neighboring scattering agents were considered to be distinct in SOCT if the maximum shift of the spectral centroid was at least half that of what the shift would be if the scattering agent was alone. The linear TFD examined was the STFT with a Hamming window ("STFT"); the Cohen's class TFDs examined were SPWVD and Morlet wavelet ("WT"); and Ideal LPFs and HPFs were used for the model-based TFDs ("Model-based"). Simple WVD did not perform well under this situation because of the strong cross-terms. Instead, the smoothed pseudo-Wigner-Villie distribution (SPWVD) was used with a smoothing Gaussian kernel applied independently in the time and frequency direction. The minimal distances needed for different TFDs to discriminate the two pulses are listed in Table 2. For reference, the structural OCT resolution (by FWHM criterion) is also listed in Table 2. The Cohen's-class TFDs had better performance than the STFT on this synthetic signal.

TABLE 2

TF resolution of TFDs on synthetic signal from second imaging scenario

|  | Structural OCT | Ideal TFD | STFT | WT | SPWVD | Model-based |
|---|---|---|---|---|---|---|
| Minimal distance (s) | 0.053 | 0.025 | 0.036 | 0.039 | 0.033 | 0.026 |

To compare the overall quality of the TFDs on the synthetic signal from the third scenario, the absorption was assumed to follow Beer's Law. The locations of the scattering agents were first identified by peak detection. Then, absorption spectra were determined from TFDs based on least-square curve fitting of TFDs from multiple scattering agents. The error function was calculated from the measured absorption spectra A'(f) and the expected absorption spectra A(f) using the formula:

$$\text{Error} = \sum_{FrequencyBand} \frac{A'(f) - A(f)}{A(f)}$$

The "Frequency Band" was defined by the 10% level criterion. The linear TFD examined was the STFT with a Hamming window ("STFT"); the Cohen's class TFDs examined were SPWVD and Morlet wavelet ("WT"); and Ideal LPFs were used for the model-based TFDs ("Model-based"). The errors for different TFDs are listed in Table 3. The model-based TFD out-performed all other TFDs. Linear TFDs were reasonably good, while all Cohen's-class TFDs gave erroneous outcomes due to cross-terms and non-ideal smoothing operations.

TABLE 3

TF resolution of TFDs on synthetic signal from third imaging scenario

|  | Ideal TFD | STFT | WT | SPWVD | Model-based |
|---|---|---|---|---|---|
| Error | 0.0% | −5.0% | −6.1% | 34.3% | 0.0% |

Example 6

Comparison of TFD Performance on Experimental SOCT Signal of Two Closely-Spaced Reflecting Interfaces Experimental SOCT signals were obtained that corresponded to the second imaging scenario in Example 5. A sample was constructed to provide two back-scattering interfaces that were spatially close and that exhibited different back-scattering spectra. Double-sided tape having a thickness of approximately 80 μm was placed between and along one edge of two 24×60 mm glass coverslips. A paper clip compressed the coverslips at the opposite edge to make a semi-closed thin gap between the two coverslips. The assembly was then turned vertically and one wedge-shaped open side was submerged into a shallow 20 mg/ml solution of the near-infrared dye of Example 2. After a few seconds, the absorbing agent solution filled the wedge-shaped space between the coverslips via capillary forces. Unlike many other water-soluble NIR absorbing agents, this dye strictly followed the Beer's Law of absorption up to very high concentrations. Even at 20 mg/ml, the absorbing agent still maintained its expected absorption spectrum. No photobleaching effect was observed with 10 mW of focused laser power over a period of 10 minutes.

The sample was imaged with a fiber-based OCT setup similar to the device of Example 1, but with the following modifications. A thin lens with a 40 mm focal length was used to minimize the effect of chromatic aberration, dispersion, and focusing. Non-linearities in the reference scanning rate were accounted for by acquiring a reference fringe pattern using a narrowband laser diode with a center wavelength around 776 nm and a bandwidth of 1 nm, and applying a data correction algorithm. This OCT system provided 4 μm axial resolution, with a 3.2 mm depth of focus (confocal parameter) in air. The interference was detected using an auto-balancing detector (Model 2007, New Focus, Inc.). The signal was amplified and filtered using an anti-aliasing low-pass filtered in a custom analog circuit. Before applying TFD analysis, the signal was bandpass filtered to remove excessive noise in the digital domain and was digitally corrected for dispersion.

Axial scans along different wedge positions (different absorbing agent thicknesses) were acquired. The sample was placed on an angle-adjustable stage such that the light reflected back from the glass/liquid interfaces was in a near-normal direction. The incident laser power was attenuated to prevent saturation at the photodetector. The interference fringe data were collected for analysis with different TFDs. The interference fringes resulting from multiple reflections (light bouncing back and forth between the two glass interfaces) were found have magnitudes at least 50 times smaller than the main interference fringes, and therefore were not used in our analysis.

The windows chosen for the STFT were Hamming windows of length corresponding to one coherence length of the incident laser. The actual distance between the two interfaces in terms of coherence lengths was measured by counting the number of fringe peaks between two pulse centers and the number of fringe peaks between the FWHM from a single pulse off of a mirror. Most of the shorter wavelengths were absent from the light reflected from the lower absorbing agent/glass interface because of the absorbing agent absorption. Blurring of the time-frequency representation as the separation of the two interfaces narrowed was observed, as would be expected from the "uncertainty principle". Specifically, when the distance between the two interfaces was less than the coherence length of the optical source, it became difficult to resolve them.

The experimental signals were subjected to TF analysis using different TFDs to compare the resolving power of the TFDs in this setting. The STFT, Scalogram, Choi-William distribution, and model-based TFDs were examined. The length of time windowing for the STFT and the Choi-William distribution was chosen to correspond to 1 µm in air. This length offered the best separation by qualitative assessment. Morlet wavelets were chosen for the Scalogram. The model for the model-based TFD was set up by assuming that the TFD of the pulse from the first interface was the same as the WVD of a pulse from a mirror ($TFD_M(z,I)$) except for a scaling factor, and that the TFD of the pulse from the second interface was the first TFD after absorbing agent absorption multiplied by another scaling factor:

$$TFD = A \times TFD_M(z,\lambda) + TFD_M(z-z_t,\lambda)\exp(-B \times \in(\lambda))$$

where A and B were the scaling factors and $z_t$ was the distance between two interfaces. This equation was digitized in z and λ to have each z point represent 0.1 µm and each λ point represent 1 nm. The term e(I) representing absorbing agent absorptivity was measured by a spectrometer. Spline interpolations were used whenever the experimentally measured data had different data points from the model. The criterion for model optimization was to search for the best A, B, and $z_t$ such that the lowest mean-square-error between the model TFD and the TFD by STFT was generated. Because it was computationally-expensive to search for three optimal parameters (A, B, $z_t$) in 3-D space, $z_t$ was first determined based on the fringe number. The parameters A and B were only searched for their optimal values in 2-D space, and then the optimal $z_t$ was determined for that A and B. The two-step recursion was repeated until results stabilized.

The TFDs from Cohen's class (the Choi-William distribution and Scalogram) had comparative performance, while both performed better than the STFT. Artifacts in the TFD plots for the Choi-William distribution were due to the cross-terms during the bilinear transformation of the signal. However, because the cross-terms were out of the primary signal bands, they could be rejected easily. Confirming the results of the simulation of Example 5, the model-based TFD had the best performance in terms of sharpness, although it may or may not have represented the true TFD.

Example 7

Comparison of TFD Performance on Experimental SOCT Signal of Homogeneous Media Containing Small Number of Scattering Agents Experimental SOCT signals were obtained that corresponded to the third imaging scenario in Example 5. Phantom samples were prepared in liquid form to provide homogeneous media containing a small amount of scattering agents. The near-infrared dye ADS830WS (American Dye Sources, Inc.) was used. Unlike the absorbing agent SDA7460 used in Example 6, this dye had a sharp absorption peak around 810 nm, which was close to the emission spectrum of the laser source. Having an absorption peak near the center of the laser source spectrum facilitated the evaluation of the performance of different TFDs. When dissolved in methanol, this absorbing agent was also very stable and did not show any photobleaching effect under 10 mW of focused laser power over a period of 10 minutes. Silica microbeads 0.33 µm in diameter (Bang Laboratories, Inc.) were used as scattering agents. The solution containing the absorbing agent and microbeads was placed inside a thin glass cuvette and imaged with the SOCT setup of Example 6. The concentrations of the absorbing agent and silica microbeads were adjusted such that the absorption loss was 5 times larger than the scattering loss at 800 nm.

Prior to SOCT imaging, the mixture was measured by a spectrometer for the combined effect of absorption loss and scattering loss. The absorption spectra were retrieved by each TFD method similar to the analysis on the third synthetic signal in Example 5, except for three additional modifications. First, a control sample containing the same concentration of microbeads, but without absorbing agent, was used for data-correction to reduce the system error. Second, because very closely-spaced scattering agents exhibit a significant spectral-interference effect, averaging of TFDs from 512 scan lines was performed to obtain the final TFDs. Third, because of the large number of data points collected (50,000 points/scan line), it was not possible to perform different TFDs directly without significant computational complexity. Therefore, taking advantage of the fact that the SOCT signals were narrow pass-band signals, data were demodulated and decimated to obtain the shortest possible analytic signals without losing frequency information within the laser source spectrum. The time window sizes for the STFT, Choi-William distributions and the model based TFDs were chosen to be four coherence length. The Morlet wavelet was used for the wavelet transform. Because no prior information was assumed, an autoregressive (AR) model using the Burg method was used for the model-based TFDs, with a model order set to 4.

Figure 10:
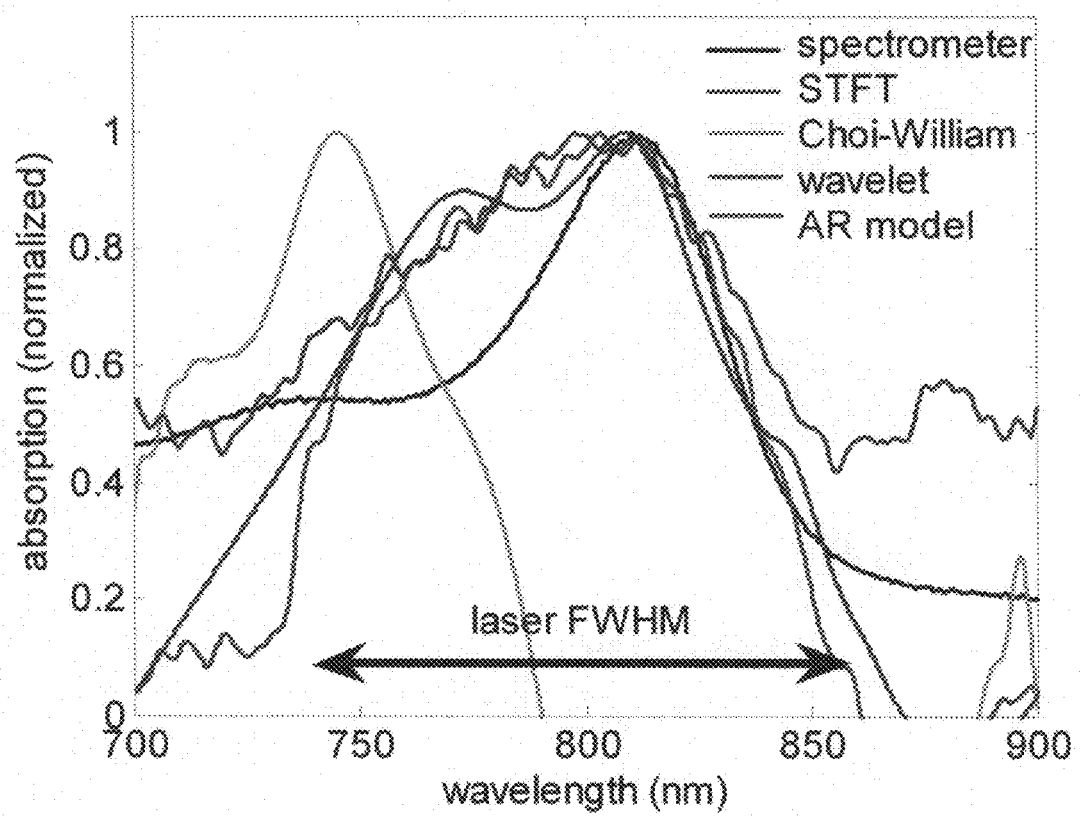
FIG. 10 is a graph of absorption spectra obtained using a variety of time-frequency distributions.

The absorption spectra obtained by different TFDs are shown in FIG. 10, together with the spectral range of the laser (FWHM). For comparison, each spectra was normalized to its respective peak value. In this SOCT imaging scenario, the STFT and the wavelet transform were the reliable methods. The model-based TFD had reasonably good performance even though no assumption was made when constructing the model. The spectrum retrieved using the Choi-William TFD was totally random. These results confirm the predictions of the simulation of Example 5.

Example 8

Spectroscopic Spectral-Domain OCT Imaging

A custom-designed and constructed multi-modality microscope was used in this study, which enabled not only OCT and SOCT, but also simultaneous multi-photon microscopy using the same optical source. The light source consisted of a frequency-doubled $Nd:YVO_4$-pumped Ti:sapphire laser with a center wavelength of 800 nm, a bandwidth of 40 nm, and an 80 MHz pulse repetition rate. This source was used as both a low-coherence source for OCT and also as an excitation source for multi-photon microscopy. The microscope objective (20×, 0.95 NA, water immersion, Olympus) had a high NA in order to achieve high lateral resolution and tight spatial confinement of the backscattered OCT signal. Dispersion in the proprietary glass of the objective was balanced digitally in the acquired image data. The interferometric setup was similar to those used in spectral-domain OCT. In our configuration, a free-space 50/50 beam splitter was used. The light in the detection arm was collimated and dispersed off a blazed diffraction grating having 830.3 grooves per millimeter. The optical spectrum was focused on a line-scan camera (L104k-2k, Basler, Inc.) which contained a 2048-element CCD array of detection elements with a maximum readout rate of 29 kHz. Digital processing of the detected signal included a Spline interpolation to make the signal more uniform, and a discrete Fourier transform on each set of 2048, 10-bit, values captured by the CCD to transform the signal from the frequency (spectral) domain into the spatial (depth) domain.

The axial PSF of the objective using spectral-domain OCT detection (coherence-gating) was measured to be 2.2 µm at FWHM. Because the source spectrum was roughly Gaussian, the sensitivity of OCT to the retro-reflected light decreased exponentially with axial distance. Note that in this system the confocal gating (confocal parameter=2.2 µm) was below the coherence gating (coherence length=7 µm) with the laser source bandwidth of 40 nm. OCT images of a calibrated U.S. Air Force test target were used to determine the high transversal resolution of this system. By use of the edge-scan definition, a transverse resolution of less than 0.9 µm was measured. To determine the sensitivity of the system, the OCT PSF from a mirror translated through the focal plane was measured with calibrated attenuation filters inserted in the sample arm. The SNR was calculated by taking the ratio between the signal power and the noise variance. With 1 mW (0 dBm) of power incident on the mirror, the measured SNR was found to be equal to 97 dB. The dynamic range within experimental image data was approximately 60 dB. Calibrated fluorescent microbeads were used to determine the axial and transverse multi-photon microscopy resolutions of our system, which were 0.8 µm and 0.5 µm, respectively. Incident optical power ranged from 1-5 mW (1 mW typical), with the higher power used to excite two-photon fluorescence from green-fluorescent protein (GFP).

The spectral-domain OCT interference fringes were acquired at 2048 pixels per OCT point, covering a potential full-array light spectral range from 740 nm to 860 nm, and which corresponded to an imaging depth of approximately 2.7 mm in air. The raw spectral-domain OCT interference was given by:

$$I(k,z)_{z=z_0} = 2[R_r R_s(k,z)_{z=z_0}]^{1/2} S(k) \cos(2k\Delta p)$$

where k is the free-space wave number, z is the depth, $R_r$ and $R_s$ are the reference reflectivity and sample reflectivity, respectively, S(k) is the source spectral density, and Dp is the optical pathlength difference at $z_0$ that is defined by the focal gating of the high NA objective. The reference reflectivity $R_r$ was assumed to be wavelength-independent. The modulation transfer function of the spectral-domain OCT system was calibrated using a mirror, and the raw spectral domain signal was re-mapped to k space using cubic Spline interpolation. The spectral-domain data then was demodulated to baseband by first taking the fast Fourier transform (FFT) to obtain the depth-dependent analytical signal, followed by the inverse FFT of the depth signal segment centered around the focal gate position. A Gaussian window of 512 points with a FWHM of 256 points was used, which corresponded to a spectral resolution of 0.5 nm.

The retrieved $R_s(k)$ at the focal plane of the OCT objective was processed by two different SOCT analysis methods. The first method was based on metameric imaging, where the scattering spectrum is divided into different sub-spectral bands. The signal intensity in each sub-spectral band was integrated to produce the intensity for one color channel. For this study, the window within the FWHM of the source spectrum was divided into three equally spaced sub-bands, and the intensity from the low-, mid-, and high-frequency bands were assigned to the red, green, and blue channels, respectively. This method represented similar information as the traditional spectral centroid method, but was more robust and more similar to the mechanism of human vision. The second method was based on spectral analysis initially proposed in LSS. The back-scattered spectra were first analyzed by the FFT, and the first peak of the FFT data was used for hue information in an HSV color scale. This peak position was related to the physical size and inter-scatterer distance of the dominant scatterers, such as the nucleus, within the focal gate at that location. The metameric method was more qualitative and suited for attenuation-based measurements in SOCT, while the spectral analysis method used in LSS was more quantitative and suited for scattering-based measurements in SOCT. These representative SOCT analysis methods were performed on spectral-domain OCT data collected from tissue and cell specimens imaged using our multi-modality microscope.

Figure 11:
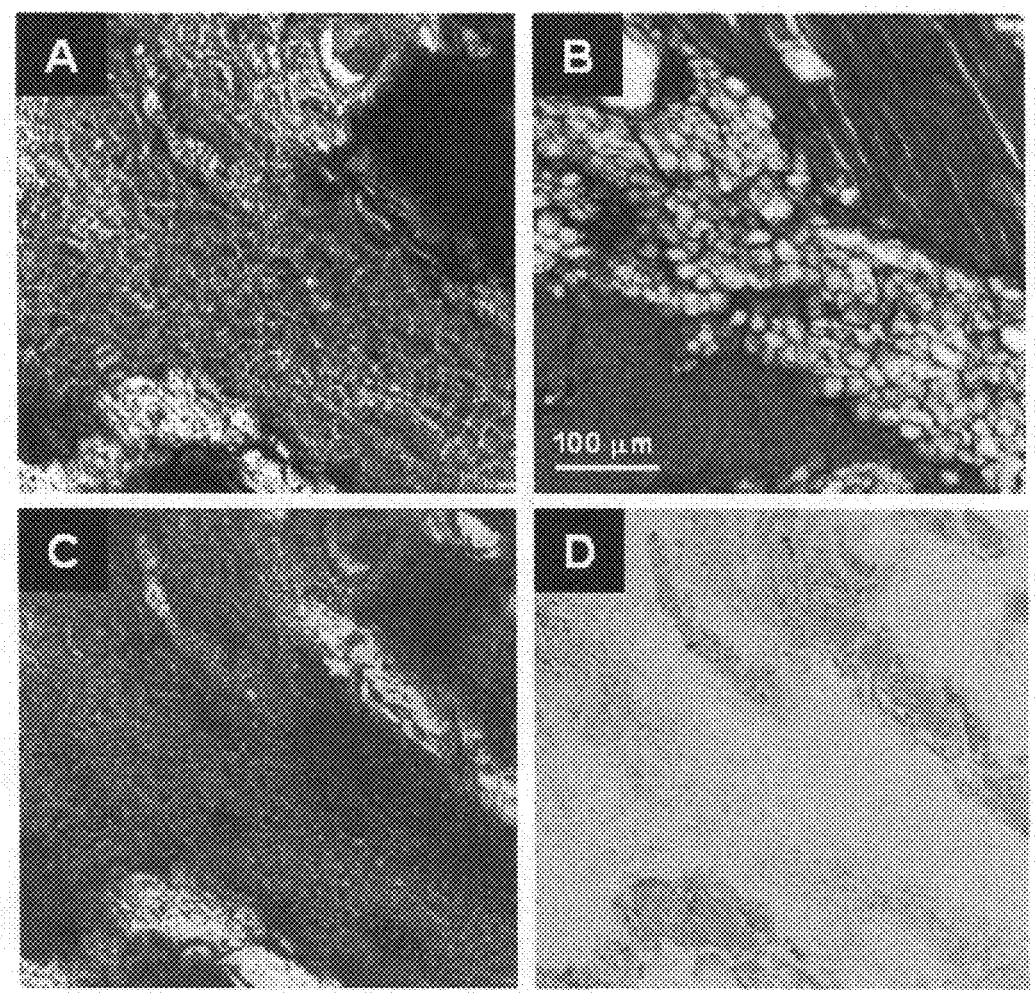
FIG. 11 is a series of images of rat mammary tissues.

FIG. 11 shows image-data acquired from mammary tissue of a rat, consisting of adjacent adipose (fat) and muscle tissue. FIG. 11B is a histological image of the tissue. The high-resolution OCT image showed individual adipocytes in the center of the image (FIG. 11A), but exhibited regions of low backscatter over the more dense muscle tissue at the upper right and lower left corners of the image, possibly due to forward scattering or polarization-dependent effects. However, compared to OCT, the SOCT analysis methods (FIGS. 11C and 11D, respectively) showed increased contrast for muscle compared to the adipose tissue where there was sufficient backscattered signal for spectral analysis. This contrast enhancement (light yellow and blue regions in FIG. 11C, and green and blue regions in FIG. 11D) was due to different scatterer sizes and scatterer organization (likely nuclei and other organelles), and was more prominent in the SOCT image based on LSS spectral analysis (FIG. 11D, green regions), which has been shown to detect changes in nuclear regions.

Figure 12:
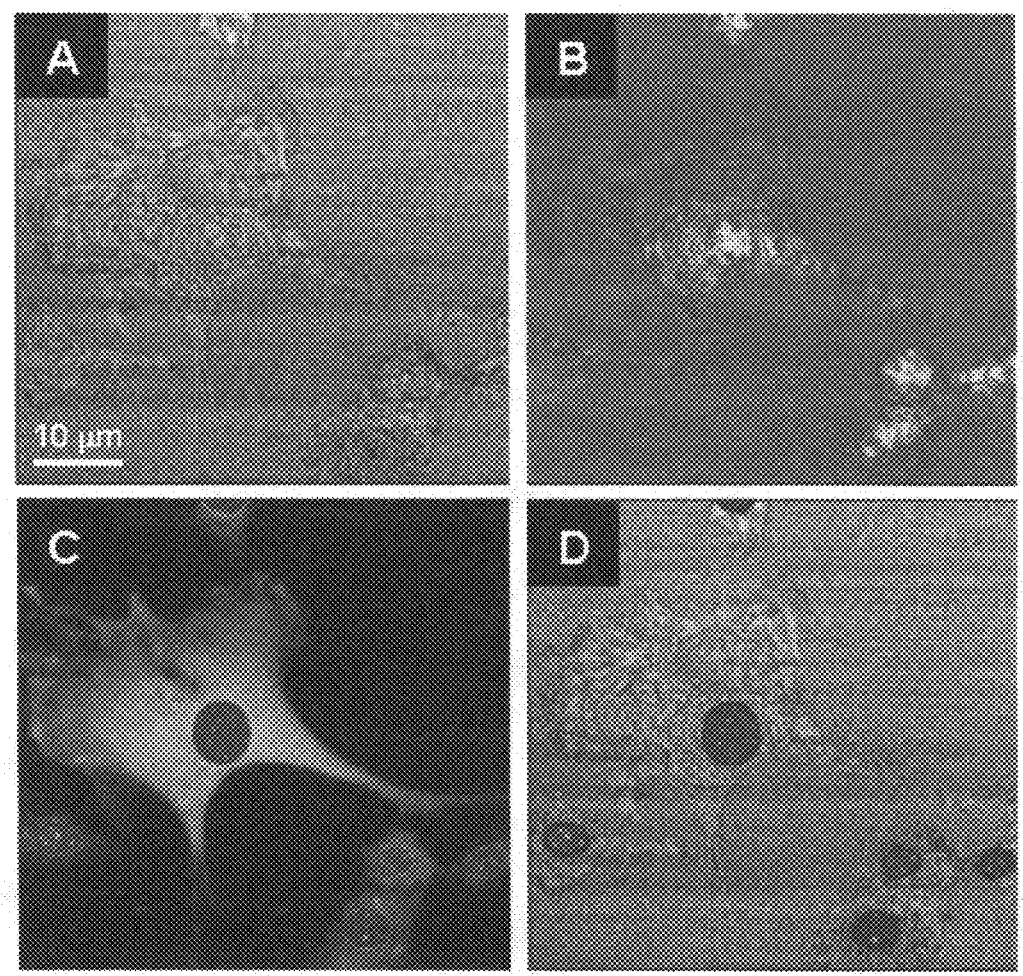
FIG. 12 is a series of single-cell images of a GFP-vinculin transfected fibroblast.

FIG. 12 shows an OCT image of live fibroblast cells in culture, and the corresponding SOCT image using LSS spectral analysis (FIGS. 12A and 12B, respectively). The first peak-positions of the FFT obtained from the modulation patterns of the back-scattered light were clearly different near the center of the cell, compared to the periphery of the cell. One possible reason for this difference was the presence a large scatterer, the nucleus, located near the center of these cultured cells. These SOCT findings were confirmed by multi-photon imaging of this cell culture, using the simultaneous multi-modality capabilities of the microscope. These transfected fibroblasts expressed GFP-labeled vinculin (a cell adhesion protein) and were co-labeled with a DNA-specific dye (Hoechst 33342) for localization of nuclei relative to the surrounding cell structures (FIG. 12C). The simultaneous multi-modality imaging afforded by the microscope enabled overlays of various image channels, as shown for OCT and the multi-photon fluorescence from the DNA/nuclear dye (FIG. 12D). The SOCT analysis information was consistent with the multi-photon imaging data in identifying the locations of the nuclei within these cells. Of the six nuclei identified in the multi-photon fluorescence image (FIG. 12C), five nuclei were clearly identified in the SOCT image (FIG. 12B, green/blue regions). The remaining cell nucleus (left-most cell) may not be identified as clearly with SOCT because this cell may have been smaller and had a flatter profile than the others, resulting in a backscattering spectrum more similar to the background.

In conclusion, spectroscopic spectral-domain OCT analysis with tight focal gating decoupled the inherent trade-off between spectral and spatial (depth) resolution. This enabled the extraction of more minute spectroscopic features from within the small imaging volumes, making localized analysis of wavelength-dependent scattering possible. Wavelength-dependent scattering and the resulting spectral modulation were information-rich processes that were dependent on both optical properties of the scatterer and the inter-scatterer spacing. Spectroscopic spectral-domain OCT was capable of enhancing contrast in various tissues and cells based solely on endogenous structures.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A method of forming an image of tissue, comprising:
   selecting at least one contrast agent, comprising at least one water-soluble, biocompatible absorbing agent having an absorption profile;
   delivering the contrast agent to the tissue;
   acquiring spectroscopic optical coherence tomography data from the tissue across a spectrum range,
   wherein the acquiring does not change the absorption profile of the absorbing agent; and
   converting the spectroscopic optical coherence tomography data into at least one image,
   wherein the at least one absorbing agent absorbs in the near-infrared region,
   the absorption profile of the absorbing agent is sharp, and
   the absorbing agent is highly absorbing in a first portion of the spectrum range and has little to no absorption in a second portion of the spectrum range.

2. The method of claim 1, wherein the at least one contrast agent further comprises at least one scattering agent.

3. The method of claim 1, wherein the selecting at least one contrast agent comprises:
   determining the optical window of the tissue;
   selecting a laser spectrum range that is within the optical window; and
   selecting at least one absorbing agent that absorbs within the laser spectrum range.

4. The method of claim 3, wherein the selecting at least one absorbing agent comprises selecting at least one absorbing agent having an absorbance spectrum that overlaps the laser spectrum range.

5. The method of claim 3, wherein the selecting at least one absorbing agent further comprises selecting at least one absorbing agent that can be delivered to the tissue.

6. The method of claim 3, further comprising selecting at least one scattering agent that scatters within the laser spectrum range.

7. The method of claim 6, wherein the selecting at least one scattering agent further comprises selecting at least one scattering agent that can be delivered to the tissue.

8. The method of claim 1, wherein the converting of the spectroscopic optical coherence tomography data into at least one image comprises:
   performing time-frequency analysis on the data;
   performing spectral/pattern analysis on the data;
   retrieving the spatial distribution of the at least one contrast agent in the tissue; and
   correlating the spatial distribution with at least one display parameter.

9. The method of claim 8, wherein the at least one contrast agent further comprises at least one scattering agent,
   the retrieving comprises retrieving the spatial distributions of the at least one absorbing agent and of the at least one scattering agent, and
   the correlating comprises correlating the spatial distributions of the least one absorbing agent and of the at least one scattering agent with at least one display parameter.

10. The method of claim 1, wherein the tissue is living.

11. A method of forming an image of tissue, comprising:
    selecting a laser spectrum range that is within an optical window;
    selecting at least one water-soluble, biocompatible absorbing agent having an absorption profile, the absorbing agent absorbing within the laser spectrum range;
    selecting at least one scattering agent that scatters within the laser spectrum range;
    delivering the at least one absorbing agent and the at least one scattering agent to the living tissue;
    acquiring spectroscopic optical coherence tomography data from the living tissue across the spectrum range,
    wherein the acquiring does not change the absorption profile of the absorbing agent;
    performing time-frequency analysis on the data;
    performing spectral/pattern analysis on the data;
    retrieving the spatial distributions of the at least one absorbing agent and of the at least one scattering agent in the living tissue; and
    correlating the spatial distributions with at least one display parameter, wherein the at least one absorbing agent absorbs in the near-infrared region,
    the absorption profile of the absorbing agent is sharp, and
    the absorbing agent is highly absorbing in a first portion of the spectrum range and has little to no absorption in a second portion of the spectrum range.

12. A method of converting spectroscopic optical coherence tomography data into at least one image, comprising:
    performing time-frequency analysis on spectroscopic optical coherence tomography data from tissue;
    performing spectral/pattern analysis on the spectroscopic optical coherence tomography data;
    retrieving the spatial distribution of at least one contrast agent in the tissue; and
    correlating the spatial distribution with at least one display parameter,
    wherein the at least one contrast agent comprises at least one absorbing agent having an absorption profile,
    the acquiring does not change the absorption profile of the absorbing agent,
    spectroscopic optical coherence tomography data is acquired across a spectrum range,
    the at least one absorbing agent absorbs in the near-infrared region,
    the absorption profile of the absorbing agent is sharp, and
    the absorbing agent is highly absorbing in a first portion of the spectrum range and has little to no absorption in a second portion of the spectrum range.

13. The method of claim 12, wherein the at least one contrast agent comprises at least one scattering agent.

14. The method of claim 12, wherein the at least one contrast agent further comprises at least one scattering agent, the retrieving comprises retrieving the spatial distributions of the at least one absorbing agent and of the at least one scattering agent, and the correlating comprises correlating the spatial distributions of the least one absorbing agent and of the at least one scattering agent with at least one display parameter.

15. A method of analyzing tissue, comprising:

delivering at least one contrast agent comprising at least one absorbing agent having an absorption profile, to the tissue; and acquiring spectroscopic optical coherence tomography data from the tissue across a spectrum range, wherein the acquiring does not change the absorption profile of the absorbing agent, the absorption profile of the absorbing agent is sharp, and the absorbing agent is highly absorbing in a first portion of the spectrum range and has little to no absorption in a second portion of the spectrum range.

16. A method of forming an image of tissue, comprising:

delivering at least one contrast agent comprising at least one absorbing agent having an absorption profile, to the tissue;

acquiring spectroscopic optical coherence tomography data from the tissue across a spectrum range, wherein the acquiring does not change the absorption profile of the absorbing agent;

separating the signal due to absorption from the signal due to scattering; and converting the spectroscopic optical coherence tomography data into at least one image, wherein the absorption profile of the absorbing agent is sharp, and the absorbing agent is highly absorbing in a first portion of the spectrum range and has little to no absorption in a second portion of the spectrum range.

17. The method of claim 16, wherein the at least one contrast agent further comprises at least one scattering agent.

18. The method of claim 16, wherein the converting the spectroscopic optical coherence tomography data into at least one image comprises:

performing time-frequency analysis on the data;

performing spectral/pattern analysis on the data;

retrieving the spatial distribution of the at least one contrast agent in the tissue; and correlating the spatial distribution with at least one display parameter.

19. The method of claim 18, wherein the at least one contrast agent further comprises at least one scattering agent, the retrieving comprises retrieving the spatial distributions of the at least one absorbing agent and of the at least one scattering agent, and the correlating comprises correlating the spatial distributions of the least one absorbing agent and of the at least one scattering agent with at least one display parameter.

20. The method of claim 16, wherein the tissue is living.

21. A method of converting spectroscopic optical coherence tomography data into at least one image, comprising:

performing time-frequency analysis on spectroscopic optical coherence tomography data from tissue;

performing spectral/pattern analysis on the spectroscopic optical coherence tomography data;

retrieving the spatial distribution of at least one contrast agent comprising at least one absorbing agent having an absorption profile, in the tissue; and correlating the spatial distribution with at least one display parameter;

wherein the performing spectral/pattern analysis on the spectroscopic optical coherence tomography data comprises separating the signal due to absorption from the signal due to scattering, the spectroscopic optical coherence tomography data is acquired across a spectrum range without changing the absorption profile of the absorbing agent, the absorption profile of the absorbing agent is sharp, and the absorbing agent is highly absorbing in a first portion of the spectrum range and has little to no absorption in a second portion of the spectrum range.

22. The method of claim 21, wherein the at least one contrast agent comprises at least one scattering agent.

23. The method of claim 21, wherein the at least one contrast agent further comprises at least one scattering agent, the retrieving comprises retrieving the spatial distributions of the at least one absorbing agent and of the at least one scattering agent, and the correlating comprises correlating the spatial distributions of the least one absorbing agent and of the at least one scattering agent with at least one display parameter.

* * * * *

UNITED STATES PATENT AND TRADEMARK OFFICE
CERTIFICATE OF CORRECTION

PATENT NO. : 7,725,169 B2
APPLICATION NO. : 11/405005
DATED : May 25, 2010
INVENTOR(S) : Stephen A. Boppart It is certified that error appears in the above-identified patent and that said Letters Patent is hereby corrected as shown below:

Page 3
First column, line 26, please delete "8994" and insert --89-94--.
First column, line 64, please delete "confiuration" and insert --configuration--.

Page 4
Second column, line 27, please put in vivo in italics.
Second column, line 43, please put in Vivo in italics.

Page 6
Second column, line 31, please put in vivo in italics.

Page 7
Column 1, line 11, please put in vivo in italics.
Column 1, line 39, please put in vitro in italics.
Column 2, line 11, please put in vivo in italics.

Page 8
Column 2, line 22, please delete "imaigng" and insert --imaging--.

Page 9
Column 1, line 10, please delete " $B^n_i$ and $D^n_i$ " and insert -- $B^i \prod_i$ and $D^i \sum_i^+$ --.

Signed and Sealed this
Tenth Day of April, 2012

David J. Kappos
*Director of the United States Patent and Trademark Office*